United States Patent
Surmeier et al.

(10) Patent No.: US 9,987,242 B2
(45) Date of Patent: Jun. 5, 2018

(54) TREATMENT OF LEVODOPA-INDUCED DYSKINESIAS

(71) Applicant: NORTHWESTERN UNIVERSITY, Evanston, IL (US)

(72) Inventors: Dalton James Surmeier, Evanston, IL (US); Weixing Shen, Wilmette, IL (US); Zhong Xie, North Riverside, IL (US)

(73) Assignee: Northwestern University, Evanston, IL (US)

( * ) Notice: Subject to any disclaimer, the term of this patent is extended or adjusted under 35 U.S.C. 154(b) by 0 days. days.

(21) Appl. No.: 15/147,092

(22) Filed: May 5, 2016

(65) Prior Publication Data

US 2016/0354330 A1 Dec. 8, 2016

Related U.S. Application Data

(60) Provisional application No. 62/157,289, filed on May 5, 2015.

(51) Int. Cl.
*A61K 31/4365* (2006.01)
*A61K 31/198* (2006.01)
*A61K 31/5025* (2006.01)

(52) U.S. Cl.
CPC ........ *A61K 31/198* (2013.01); *A61K 31/4365* (2013.01); *A61K 31/5025* (2013.01)

(58) Field of Classification Search
None
See application file for complete search history.

(56) References Cited

U.S. PATENT DOCUMENTS

| | | | |
|---|---|---|---|
| 4,657,760 A | 4/1987 | Kung et al. | |
| 5,206,344 A | 4/1993 | Katre et al. | |
| 5,225,212 A | 7/1993 | Martin et al. | |
| 7,531,541 B2 | 5/2009 | Conn et al. | |
| 8,034,806 B2 | 10/2011 | Conn et al. | |
| 8,207,155 B2 | 6/2012 | Lindsley et al. | |
| 8,211,933 B2 | 7/2012 | Lindsley et al. | |
| 8,431,700 B2 | 4/2013 | Lindsley et al. | |
| 8,436,019 B2 | 5/2013 | Lindsley et al. | |
| 8,497,289 B2 | 7/2013 | Lindsley et al. | |
| 8,501,757 B2 | 8/2013 | Conn et al. | |
| 8,569,308 B2 | 10/2013 | Conn et al. | |
| 8,592,422 B2 | 11/2013 | Conn et al. | |
| 8,598,345 B2 | 12/2013 | Conn et al. | |
| 8,658,650 B2 | 2/2014 | Conn et al. | |
| 8,697,691 B2 | 4/2014 | Conn et al. | |
| 8,697,888 B2 | 4/2014 | Lindsley et al. | |
| 8,703,946 B2 | 4/2014 | Conn et al. | |
| 8,710,074 B2 | 4/2014 | Conn et al. | |
| 8,759,377 B2 | 6/2014 | Conn et al. | |
| 8,772,509 B2 | 7/2014 | Lindsley et al. | |
| 8,779,157 B2 | 7/2014 | Conn et al. | |
| 8,796,295 B2 | 8/2014 | Conn et al. | |
| 8,853,237 B2 | 10/2014 | Conn et al. | |
| 8,853,392 B2 | 10/2014 | Conn et al. | |
| 8,865,725 B2 | 10/2014 | Conn et al. | |
| 8,901,125 B2 | 12/2014 | Conn et al. | |
| 8,912,336 B2 | 12/2014 | Conn et al. | |
| 8,916,584 B2 | 12/2014 | Conn et al. | |
| 8,969,389 B2 | 3/2015 | Conn et al. | |
| 9,012,445 B2 | 4/2015 | Lindsley et al. | |
| 9,029,366 B2 | 5/2015 | Conn et al. | |
| 9,029,563 B2 | 5/2015 | Lindsley et al. | |
| 9,056,875 B2 | 6/2015 | Lindsley et al. | |
| 9,056,876 B2 | 6/2015 | Conn et al. | |
| 9,073,935 B2 | 7/2015 | Lindsley et al. | |
| 9,085,562 B2 | 7/2015 | Conn et al. | |
| 9,090,632 B2 | 7/2015 | Conn et al. | |
| 9,108,963 B2 | 8/2015 | Conn et al. | |
| 9,163,015 B2 | 10/2015 | Conn et al. | |
| 9,180,192 B2 | 11/2015 | Conn et al. | |
| 9,192,603 B2 | 11/2015 | Conn et al. | |
| 9,255,103 B2 | 2/2016 | Conn et al. | |
| 2003/0109504 A1* | 6/2003 | Brotchie ................ | A61K 31/00 514/150 |
| 2003/0190504 A1 | 6/2003 | Brotchie et al. | |
| 2011/0124663 A1 | 5/2011 | Conn et al. | |
| 2012/0245153 A1 | 9/2012 | Conn et al. | |
| 2012/0245185 A1 | 9/2012 | Conn et al. | |
| 2013/0040944 A1 | 2/2013 | Conn et al. | |
| 2013/0065895 A1 | 3/2013 | Conn et al. | |
| 2013/0079366 A1 | 3/2013 | Conn et al. | |
| 2013/0096110 A1 | 4/2013 | Conn et al. | |
| 2013/0123236 A1 | 5/2013 | Lindsley et al. | |
| 2013/0158078 A1 | 6/2013 | Conn et al. | |

(Continued)

FOREIGN PATENT DOCUMENTS

WO WO2004/097009 11/2004
WO WO2005/075465 8/2005

OTHER PUBLICATIONS

Nickols, H. et al., Neurobiol. Dis 2014 vol. 61, pp. 55-71.*
Bubser, M. et al., ACS Chem. Neurosci. 2014 vol. 5 pp. 920-942.*
Alexander et al., Remote control of neuronal activity in transgenic mice expressing evolved G protein-coupled receptors. Neuron. Jul. 16, 2009;63(1):27-39.
Armbruster et al., Evolving the lock to fit the key to create a family of G protein-coupled receptors potently activated by an inert ligand. Proc Natl Acad Sci U S A. Mar. 20, 2007;104(12):5163-8.
Augustin et al., Cyclic AMP and afferent activity govern bidirectional synaptic plasticity in striatopallidal neurons. J Neurosci. May 7, 2014;34(19):6692-9.
Belujon et al., Aberrant striatel plasticity is specifically associated with dyskinesia following levodopa treatment. Mov Disord. Aug. 15, 2010;25(11):1568-76.
Bernard et al., Phenotypical characterization of the rat striatel neurons expressing muscarinic receptor genes. J Neurosci. Sep. 1992;12(9):3591-600.

(Continued)

*Primary Examiner* — Heidi Reese

(74) *Attorney, Agent, or Firm* — Casimir Jones SC; David W. Staple

(57) ABSTRACT

Provided herein are compositions and methods for the treatment and prevention of levodopa-induced dyskinesias (LID). In particular, M4 muscarinic receptor (M4R) positive allosteric modulators (PAMs) are administered to reduce dyskinetic behavior.

14 Claims, 19 Drawing Sheets

(56) References Cited

U.S. PATENT DOCUMENTS

| | | |
|---|---|---|
| 2013/0178458 A1 | 7/2013 | Lindsley et al. |
| 2013/0252943 A1 | 9/2013 | Conn et al. |
| 2013/0261107 A1 | 10/2013 | Conn et al. |
| 2013/0338154 A1 | 12/2013 | Conn et al. |
| 2013/0345203 A1 | 12/2013 | Conn et al. |
| 2013/0345204 A1 | 12/2013 | Conn et al. |
| 2013/0345205 A1 | 12/2013 | Conn et al. |
| 2013/0345206 A1 | 12/2013 | Conn et al. |
| 2014/0057870 A1 | 2/2014 | Conn et al. |
| 2014/0194471 A1 | 7/2014 | Lindsley et al. |
| 2014/0206676 A1 | 7/2014 | Lindsley et al. |
| 2014/0206707 A1 | 7/2014 | Conn et al. |
| 2014/0213593 A1 | 7/2014 | Conn et al. |
| 2014/0288084 A1 | 9/2014 | Lindsley et al. |
| 2014/0329838 A1 | 11/2014 | Conn et al. |
| 2014/0357615 A1 | 12/2014 | Conn et al. |
| 2014/0364409 A1 | 12/2014 | Lindsley et al. |
| 2015/0018309 A1 | 1/2015 | Lindsley et al. |
| 2015/0216863 A1 | 8/2015 | Conn et al. |
| 2015/0266866 A1 | 9/2015 | Conn et al. |
| 2015/0361081 A1 | 12/2015 | Conn et al. |
| 2016/0096833 A1 | 4/2016 | Emmitte et al. |
| 2016/0102090 A1 | 4/2016 | Lindsley et al. |

OTHER PUBLICATIONS

Bonsi et al., Loss of muscarinic autoreceptor function impairs long-term depression but not long-term potentiation in the striatum. J Neurosci. Jun. 11, 2008;28(24):6258-63.

Brady et al., Centrally active allosteric potentiators of the M4 muscarinic acetylcholine receptor reverse amphetamine-induced hyperlocomotor activity in rats. J Pharmacol Exp Ther. Dec. 2008;327(3):941-53.

Bubser et al, Selective activation of M4 muscarinic acetylcholine receptors reverses MK-801-induced behavioral impairments and enhances associative learning in rodents. ACS Chem Neurosci. Oct. 15, 2014;5(10):920-42.

Calabresi et al., Dopamine-mediated regulation of corticostriatal synaptic plasticity. Trends Neurosci. May 2007;30(5):211-9.

Caulfield et al., International Union of Pharmacology. XVII. Classification of muscarinic acetylcholine receptors. Pharmacol Rev. Jun. 1998;50(2):279-90.

Cenci et al., Maladaptive striatel plasticity in L-DOPA-induced dyskinesia. Prog Brain Res. 2010;183:209-33.

Cenci et al., Ratings of L-DOPA-induced dyskinesia in the unilateral 6-OHDA lesion model of Parkinson's disease in rats and mice. Curr Protoc Neurosci. Oct. 2007;Chapter 9:Unit 9.25.

Cenci, Dopamine dysregulation of movement control in L-DOPA-induced dyskinesia. Trends Neurosci. May 2007;30(5):236-43.

Cerovic et al., Derangement of Ras-guanine nucleotide-releasing factor 1 (Ras-GRF1) and extracellular signal-regulated kinase (ERK) dependent striatel plasticity in L-DOPA-induced dyskinesia. Biol Psychiatry. Jan. 15, 2015;77(2):106-15.

Chalifoux et al., GABAB receptors modulate NMDA receptor calcium signals in dendritic spines. Neuron. Apr. 15, 2010;66(1):101-13.

Chan et al., Strain-specific regulation of striatel phenotype in Drd2-eGFP BAC transgenic mice. J Neurosci. Jul. 4, 2012;32(27):9124-32.

Dencker et al., An allosteric enhancer of M4 muscarinic acetylcholine receptor function inhibits behavioral and neurochemical effects of cocaine. Psychopharmacology (Berl). Nov. 2012;224(2):277-87.

Di Chiara et al., Modulatory functions of neurotransmitters in the striatum: ACh/dopamine/NMDA interactions. Trends Neurosci. Jun. 1994;17(6):228-33.

Ding et al., Thalamic gating of corticostriatal signaling by cholinergic interneurons. Neuron. Jul. 29, 2010;67(2):294-307.

Fasano et al., Inhibition of Ras-guanine nucleotide-releasing factor 1 (Ras-GRF1) signaling in the striatum reverts motor symptoms associated with L-dopa-induced dyskinesia.Proc Natl Acad Sci U S A. Dec. 14, 2010;107(50):21824-9.

Ferguson et al., Transient neuronal inhibition reveals opposing roles of indirect and direct pathways in sensitization. Nat Neurosci. Jan. 2011;14(1):22-4.

Feyder et al., L-DOPA-Induced dyskinesia and abnormal signaling in striatel medium spiny neurons: focus on dopamine D1 receptor-mediated transmission. Front Behav Neurosci. Oct. 24, 2011;5:71.

Fino et al., Distinct coincidence detectors govern the corticostriatal spike timing-dependent plasticity. J Physiol. Aug. 15, 2010;588(Pt 16):3045-62.

Francardo et al., Impact of the lesion procedure on the profiles of motor impairment and molecular responsiveness to L-DOPA in the 6-hydroxydopamine mouse model of Parkinson's disease. Neurobiol Dis. Jun. 2011;42(3):327-40.

Gerfen et al., Modulation of striatel projection systems by dopamine. Annu Rev Neurosci. 2011;34:441-66.

Gold et al., Regulators of G-protein signaling (RGS) proteins: region-specific expression of nine subtypes in rat brain.J Neurosci. Oct. 15, 1997;17(20):8024-37.

Gomeza et al., Enhancement of D1 dopamine receptor-mediated locomotor stimulation in M4 muscarinic acetylcholine receptor knockout mice. Proc Natl Acad Sci U S A. Aug. 31, 1999;96(18):10483-8.

Gong et al., A gene expression atlas of the central nervous system based on bacterial artificial chromosomes. Nature. Oct. 30, 2003;425(6961):917-25.

Heiman et al., Molecular adaptations of striatel spiny projection neurons during levodopa-induced dyskinesia. Proc Natl Acad Sci U S A. Mar. 25, 2014;111(12):4578-83.

Hernández-Flores et al., Modulation of direct pathway striatel projection neurons by muscarinic $M_4$- type receptors. Neuropharmacology. Feb. 2015;89:232-44.

Hersch et al., Distribution of m1-m4 muscarinic receptor proteins in the rat striatum: light and electron microscopic immunocytochemistry using subtype-specific antibodies.J Neurosci. May 1994;14(5 Pt 2):3351-6.

Hervé, Identification of a specific assembly of the g protein golf as a critical and regulated module of dopamine and adenosine-activated cAMP pathways in the striatum. Front Neuroanat. Aug. 5, 2011;5:48.

Higley et al., Cholinergic modulation of multivesicular release regulates striatel synaptic potency and integration. Nat Neurosci. Sep. 2009;12(9):1121-8.

Higley et al., Competitive regulation of synaptic Ca2+ influx by D2 dopamine and A2A adenosine receptors. Nat Neurosci. Aug. 2010;13(8):958-66.

Izzo et al., Cholinergic synaptic input to different parts of spiny striatonigral neurons in the rat. J Comp Neurol. Mar. 8, 1988;269(2):219-34.

Jenner Molecular mechanisms of L-DOPA-induced dyskinesia. Nat Rev Neurosci. Sep. 2008;9(9):665-77.

Jeon et al., A subpopulation of neuronal M4 muscarinic acetylcholine receptors plays a critical role in modulating dopamine-dependent behaviors. J Neurosci. Feb. 10, 2010;30(6):2396-405.

Kozorovitskiy et al., Recurrent network activity drives striatal synaptogenesis. Nature. May 13, 2012;485(7400):646-50.

Krapivinsky et al., The NMDA receptor is coupled to the ERK pathway by a direct interaction between NR2B and RasGRF1. Neuron. Nov. 13, 2003;40(4):775-84.

Kreitzer et al., Endocannabinoid-mediated rescue of striatal LTD and motor deficits in Parkinson's disease models. Nature. Feb. 8, 2007;445(7128):643-7.

Kurz et al., A53T-alpha-synuclein overexpression impairs dopamine signaling and striatel synaptic plasticity in old mice. PLoS One. Jul. 7, 2010;5(7):e11464.

Lee et al., Regulation of distinct AMPA receptor phosphorylation sites during bidirectional synaptic plasticity. Nature. Jun. 22, 2000;405(6789):955-9.

Lerner et al., Endocannabinoid signaling mediates psychomotor activation by adenosine A2A antagonists. J Neurosci. Feb. 10, 2010;30(6):2160-4.

(56) References Cited

OTHER PUBLICATIONS

Lerner et al., Neuromodulatory control of striatel plasticity and behavior. Curr Opin Neurobiol. Apr. 2011;21(2):322-7.
Lerner et al., RGS4 is required for dopaminergic control of striatal LTD and susceptibility to parkinsonian motor deficits. Neuron. Jan. 26, 2012;73(2):347-59.
Loudon et al., SB 202026: a novel muscarinic partial agonist with functional selectivity for M1 receptors. J Pharmacol Exp Ther. Dec. 1997;283(3):1059-68.
Lovinger, Neurotransmitter roles in synaptic modulation, plasticity and learning in the dorsal striatum. Neuropharmacology. Jun. 2010;58(7):951-61.
Maia et al., From reinforcement learning models to psychiatric and neurological disorders. Nat Neurosci. Feb. 2011;14(2):154-62.
Murphy et al., Phosphorylation of Ser1166 on GluN2B by PKA is critical to synaptic NMDA receptor function and Ca2+ signaling in spines. J Neurosci. Jan. 15, 2014;34(3):869-79.
Nazzaro et al., SK channel modulation rescues striatel plasticity and control over habit in cannabinoid tolerance. Nat Neurosci. Jan. 8, 2012;15(2):284-93.
Nickols et al., Development of allosteric modulators of GPCRs for treatment of CNS disorders. Neurobiol Dis. Jan. 2014;61:55-71.
Otmakhova et al., D1/D5 dopamine receptors inhibit depotentiation at CA1 synapses via cAMP-dependent mechanism. J Neurosci. Feb. 15, 1998;18(4):1270-9.
Pancani et al., M4 mAChR-mediated modulation of glutamatergic transmission at corticostriatal synapses. ACS Chem Neurosci. Apr. 16, 2014;5(4):318-24.
Park et al., Essential role of presynaptic NMDA receptors in activity-dependent BDNF secretion and corticostriatal LTP. Neuron. Dec. 3, 2014;84(5):1009-22.
Pascoli et al., Reversal of cocaine-evoked synaptic potentiation resets drug-induced adaptive behaviour. Nature. Dec. 7, 2011;481(7379):71-5.
Pavón et al., ERK phosphorylation and FosB expression are associated with L-DOPA-induced dyskinesia in hemiparkinsonian mice. Biol Psychiatry. Jan. 1, 2006;59(1):64-74.
Pawlak et al., Dopamine receptor activation is required for corticostriatal spike-timing-dependent plasticity. J Neurosci. Mar. 5, 2008;28(10):2435-46.
Picconi et al., Loss of bidirectional striatel synaptic plasticity in L-DOPA- induced dyskinesia. Nat Neurosci. May 2003;6(5):501-6.
Picconi et al., Plastic and behavioral abnormalities in experimental Huntington's disease: a crucial role for cholinergic interneurons. Neurobiol Dis. Apr. 2006;22(1):143-52.
Plotkin et al., Impaired TrkB receptor signaling underlies corticostriatal dysfunction in Huntington's disease. Neuron. Jul. 2, 2014;83(1):178-88.
Rogan et al., Remote control of neuronal signaling. Pharmacol Rev. Jun. 2011;63(2):291-315.
Sánchez et al., Muscarinic inhibition of hippocampal and striatel adenylyl cyclase is mainly due to the M4 receptor. Neurochem Res. Aug. 2009;34(8):1363-71.
Santini et al., Critical involvement of cAMP/DARPP-32 and extracellular signal-regulated protein kinase signaling in L-DOPA-induced dyskinesia. J Neurosci. Jun. 27, 2007;27(26):6995-7005.
Santini et al., L-DOPA activates ERK signaling and phosphorylates histone H3 in the striatonigral medium spiny neurons of hemiparkinsonian mice. J Neurochem. Feb. 2009;108(3):621-33.
Schallert et al., CNS plasticity and assessment of forelimb sensorimotor outcome in unilateral rat models of stroke, cortical ablation, parkinsonism and spinal cord injury. Neuropharmacology. Mar. 3, 2000;39(5):777-87.
Shen et al., Cholinergic modulation of Kir2 channels selectively elevates dendritic excitability in striatopallidal neurons. Nat Neurosci. Nov. 2007;10(11):1458-66.
Shen et al., Cholinergic suppression of KCNQ channel currents enhances excitability of striatel medium spiny neurons.J Neurosci. Aug. 10, 2005;25(32):7449-58.
Shen et al., Dichotomous dopaminergic control of striatel synaptic plasticity. Science. Aug. 8, 2008;321(5890):848-51.
Shen et al., M4 Muscarinic Receptor Signaling Ameliorates Striatal Plasticity Deficits in Models of L-DOPA-Induced Dyskinesia. Neuron. Nov. 18, 2015;88(4):762-73.
Shirey et al., An allosteric potentiator of M4 mAChR modulates hippocampal synaptic transmission. Nat Chem Biol. Jan. 2008;4(1):42-50.
Shuen et al., Drd1a-tdTomato BAC transgenic mice for simultaneous visualization of medium spiny neurons in the direct and indirect pathways of the basal ganglia. J Neurosci. Mar. 12, 2008;28(11):2681-5.
Skeberdis et al., Protein kinase A regulates calcium permeability of NMDA receptors. Nat Neurosci. Apr. 2006;9(4):501-10.
Surmeier et al., Dopamine and synaptic plasticity in dorsal striatel circuits controlling action selection. Curr Opin Neurobiol. Dec. 2009;19(6):621-8.
Sweatt Mitogen-activated protein kinases in synaptic plasticity and memory. Curr Opin Neurobiol. Jun. 2004;14(3):311-7.
Thiele et al., Selective loss of bi-directional synaptic plasticity in the direct and indirect striatal output pathways accompanies generation of parkinsonism and L-DOPA induced dyskinesia in mouse models. Neurobiol Dis. Nov. 2014;71:334-44.
Threlfell et al., Striatel muscarinic receptors promote activity dependence of dopamine transmission via distinct receptor subtypes on cholinergic interneurons in ventral versus dorsal striatum. J Neurosci. Mar. 3, 2010;30(9):3398-408.
Tillerson et al., Forced limb-use effects on the behavioral and neurochemical effects of 6- hydroxydopamine. J Neurosci. Jun. 15, 2001;21(12):4427-35.
Tozzi et al., The distinct role of medium spiny neurons and cholinergic interneurons in the $D_2/A_2A$ receptor interaction in the striatum: implications for Parkinson's disease. J Neurosci. Feb. 2, 2011;31(5):1850-62.
Wang et al., Dopaminergic control of corticostriatal long-term synaptic depression in medium spiny neurons is mediated by cholinergic interneurons. Neuron. May 4, 2006;50(3):443-52.
Wess et al., Novel designer receptors to probe GPCR signaling and physiology. Trends Pharmacol Sci. Jul. 2013;34(7):385-92.
Westin et al., Spatiotemporal pattern of striatal ERK1/2 phosphorylation in a rat model of L-DOPA- induced dyskinesia and the role of dopamine D1 receptors. Biol Psychiatry. Oct. 1, 2007;62(7):800-10.
Wickens et al., Neural mechanisms of reward- related motor learning. Curr Opin Neurobiol. Dec. 2003;13(6):685-90.
Wu et al., Input- and cell-type-specific endocannabinoid-dependent LTD in the striatum. Cell Rep. Jan. 6, 2015;10(1):75-87.
Yagishita et al., A critical time window for dopamine actions on the structural plasticity of dendritic spines. Science. Sep. 26, 2014;345(6204):1616-20.
Yin et al., Frequency-specific and D2 receptor-mediated inhibition of glutamate release by retrograde endocannabinoid signaling. Proc Natl Acad Sci U S A. May 23, 2006;103(21):8251-6.
Yin et al., The role of the basal ganglia in habit formation. Nat Rev Neurosci. Jun. 2006;7(6):464-76.
Zhu et al., Ras and Rap control AMPA receptor trafficking during synaptic plasticity. Cell. Aug. 23, 2002;110(4):443-55.
Zhuo et al., A selective role of calcineurin aalpha in synaptic depotentiation in hippocampus. Proc Natl Acad Sci USA 96, 4650-4655.
International Search Report and Written Opinion for PCT/US2016/030894, dated Aug. 5, 2016, 11 pages.

* cited by examiner

FIG. 1A  FIG. 1B  FIG. 1C
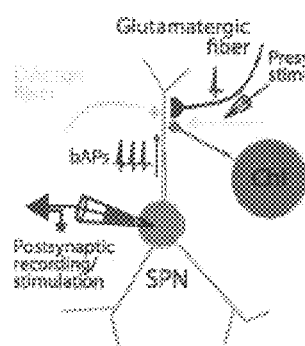
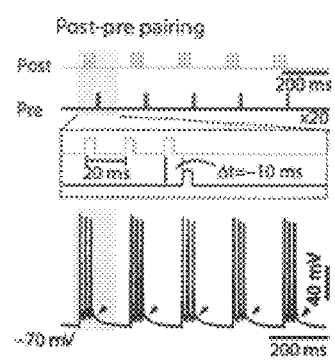
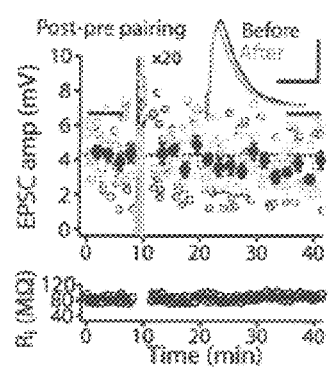
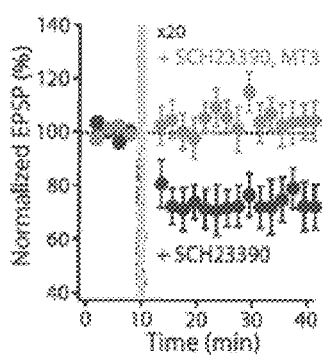
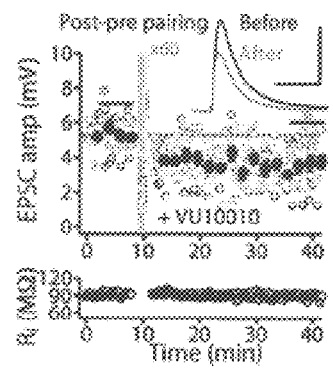
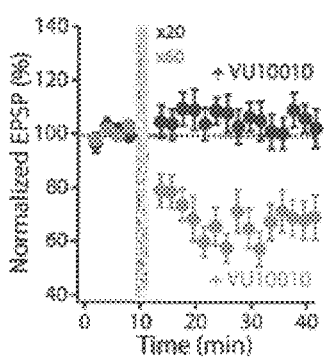
FIG. 1D  FIG. 1E  FIG. 1F FIG. 2A 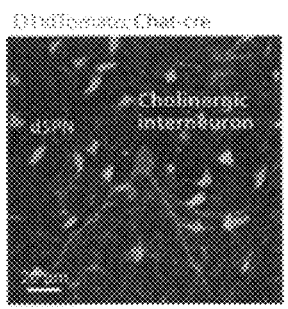 FIG. 2B 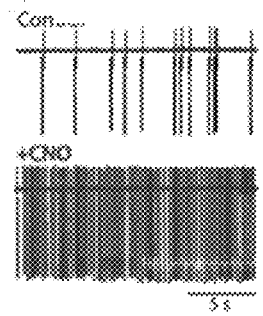 FIG. 2C 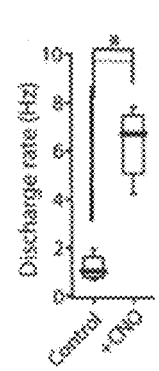
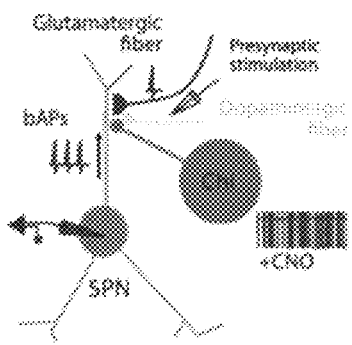
FIG. 2D
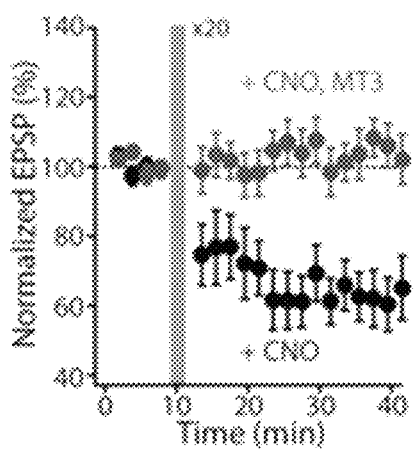
FIG. 2E
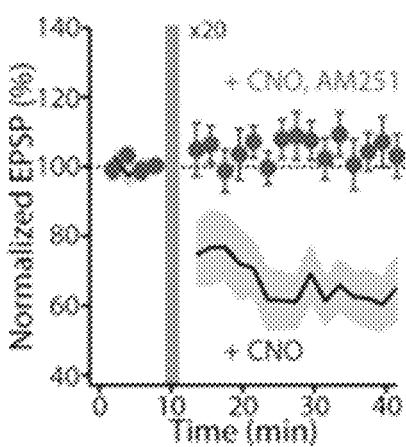
FIG. 2F

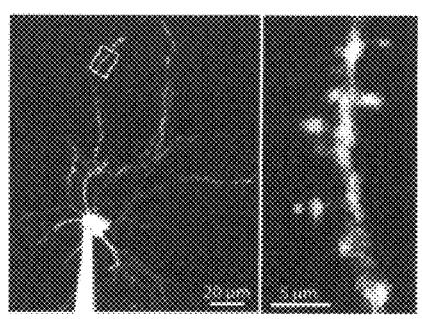
FIG. 3A
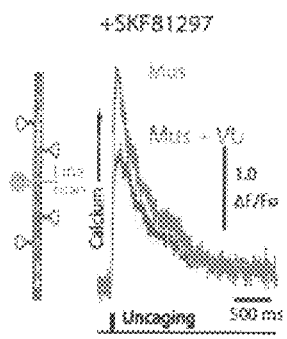
FIG. 3B
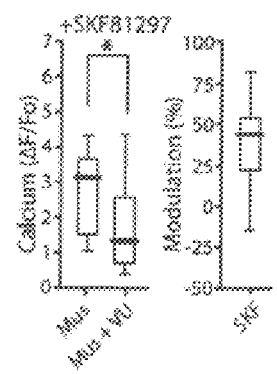
FIG. 3C
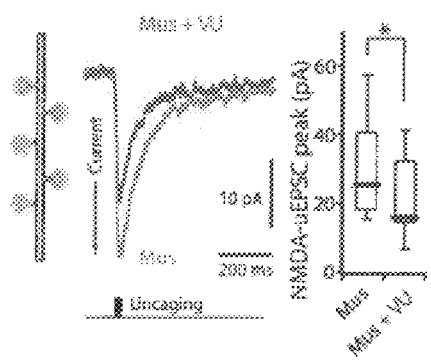
FIG. 3D
FIG. 3E
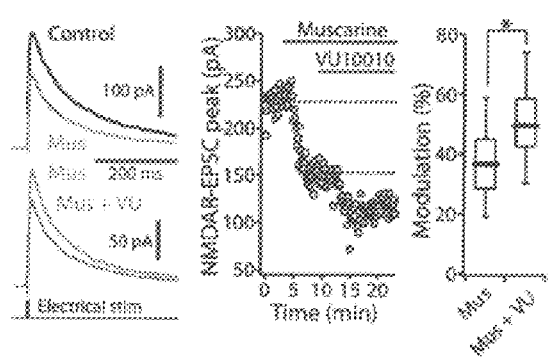
FIG. 3F FIG. 5A
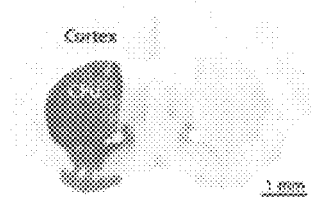
FIG. 5B
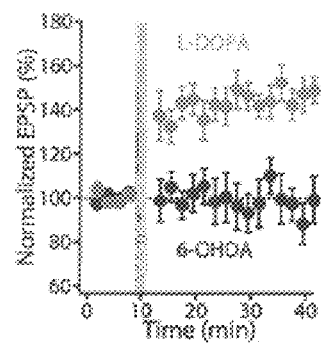
FIG. 5C
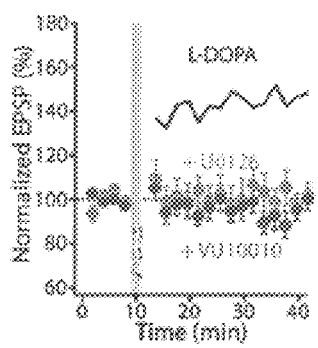
FIG. 5D
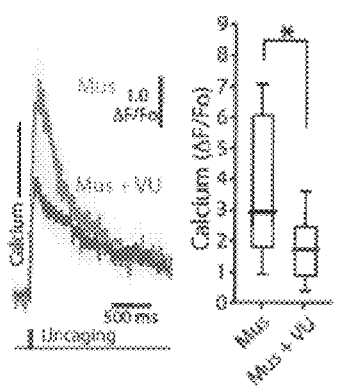
FIG. 5E
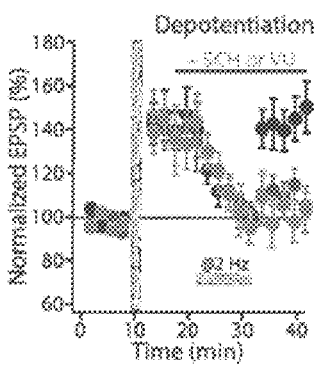
FIG. 5F FIG. 6A
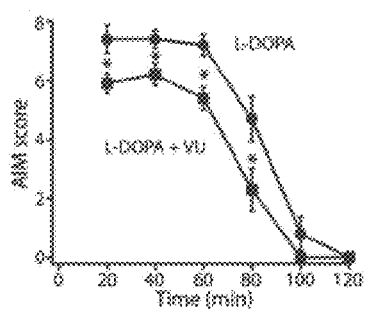
FIG. 6B
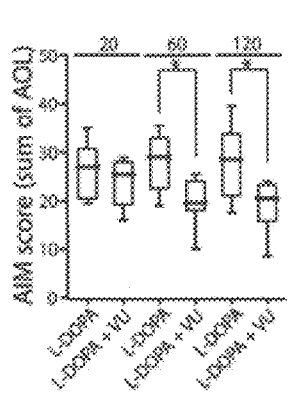
FIG. 6C
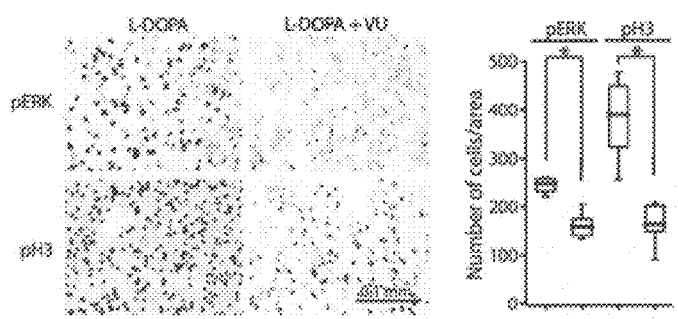
FIG. 6D
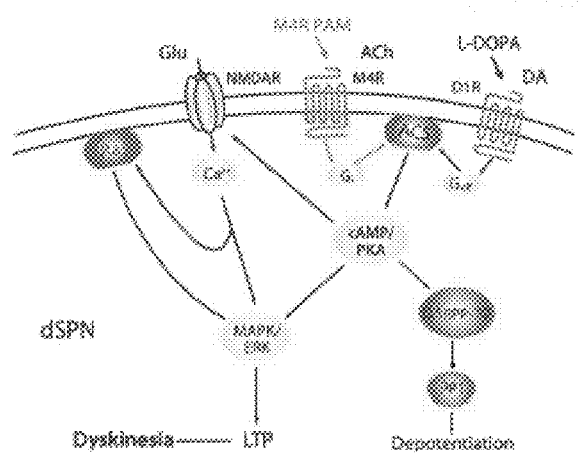
FIG. 6E

VU 10010

Chemical Name: 3-Amino-N-[(4-chlorophenyl)methyl]-4,6-dimethylthieno[2,3-b]pyridine-2-carboxamide

VU 152100

Alternative Name: ML 108
Chemical Name: 3-Amino-N-(4-methoxybenzyl)-4,6-dimethylthieno[2,3-b]pyridine carboxamide

VU0467154

FIG. 17A
FIG. 17B
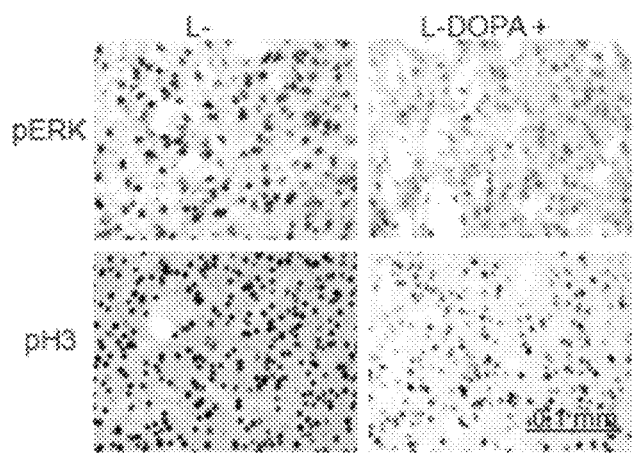
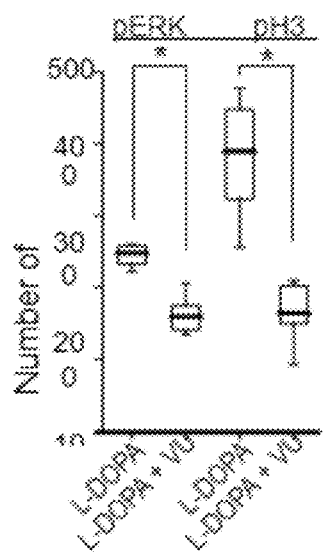

FIG. 19A
FIG. 19B
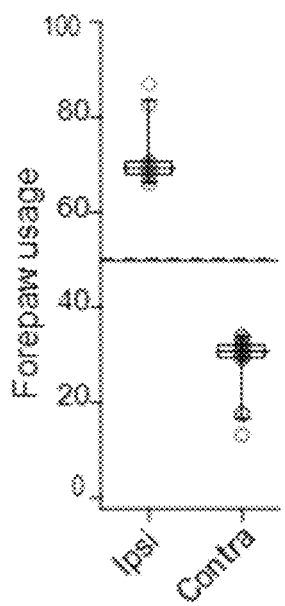
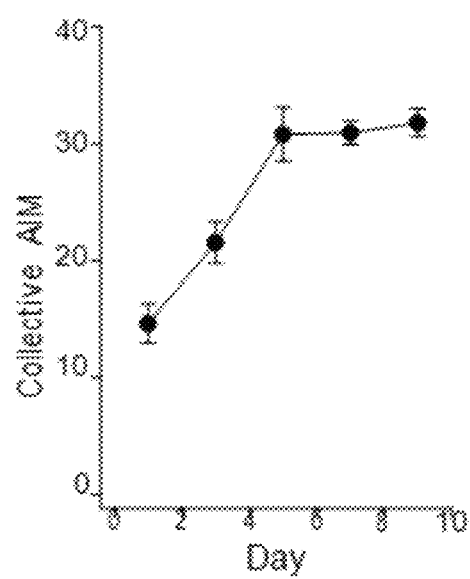

TREATMENT OF LEVODOPA-INDUCED DYSKINESIAS

CROSS REFERENCE TO RELATED APPLICATIONS

The present invention claims priority to U.S. Provisional Patent Application 62/157,289 filed May 5, 2015, which is incorporated by reference in its entirety.

STATEMENT REGARDING FEDERAL FUNDING

This invention was made with government support under grant numbers P50 MH074866 and R01 NS034696 awarded by the National Institutes of Health. The government has certain rights in the invention.

FIELD

Provided herein are compositions and methods for the treatment and prevention of levodopa-induced dyskinesias (LID). In particular, M4 muscarinic receptor (M4R) positive allosteric modulators (PAMs) are administered to reduce dyskinetic behavior.

BACKGROUND

The striatum is a key component of the basal ganglia circuitry controlling action selection and habit learning (Maia and Frank, 2011; Yin and Knowlton, 2006; herein incorporated by reference in their entireties). It is widely assumed that activity-dependent alterations in the strength of corticostriatal glutamatergic synapses formed on principal spiny projection neurons (SPNs) underlies striatal learning (Lerner and Kreitzer, 2011; Surmeier et al., 2009; Wickens et al., 2003; herein incorporated by reference in their entireties). Not only are these synapses important for normal learning, their dysregulation has been implicated in a number of psychomotor diseases, including Parkinson's disease (PD) (Gerfen and Surmeier, 2011; Kreitzer and Malenka, 2007; Kurz et al., 2010; Shen et al., 2008; herein incorporated by reference in their entireties).

One of the most important modulators of corticostriatal synapses is dopamine (DA) (Calabresi et al., 2007; Gerfen and Surmeier, 2011; Kreitzer and Malenka, 2007; Lovinger, 2010; Shen et al., 2008; herein incorporated by reference in their entireties). By virtue of their differential expression of G-protein linked DA receptors, striatal indirect pathway SPNs (iSPNs) and direct pathway SPNs (dSPNs) respond to DA in contrasting ways. In D2 receptor (D2R) expressing iSPNs, DA promotes the induction of Hebbian long-term depression (LTD) at corticostriatal synapses and opposes A2a adenosine receptor (A2aR) mediated induction of long-term potentiation (LTP) (Shen et al., 2008; Surmeier et al., 2009; herein incorporated by reference in their entireties). This is accomplished by bidirectionally regulating adenylyl cyclase (AC) through Gi-coupled D2Rs and Golf-coupled A2aRs (Augustin et al., 2014; Higley and Sabatini, 2010; Lerner et al., 2010; herein incorporated by reference in their entireties).

In dSPNs, Golf-coupled D1 DA receptors (D1Rs) are necessary for the induction of LTP. D1R signaling also disrupts the induction of Hebbian LTD (Fino et al., 2010; Pawlak and Kerr, 2008; Shen et al., 2008; Yagishita et al., 2014; herein incorporated by reference in their entireties). But it is unclear whether there is a receptor that is homologous to the D2R in dSPNs that promotes LTD and opposes LTP induction.

The Gi-coupled M4 muscarinic receptor (M4R) is the most abundant striatal muscarinic receptor and it is preferentially expressed in dSPNs where it is clustered near axospinous glutamatergic synapses (Bernard et al., 1992; Di Chiara et al., 1994; Hersch et al., 1994; Izzo and Bolam, 1988; herein incorporated by reference in their entireties). Giant cholinergic interneurons (ChIs) have dense terminal fields that overlap those of DA neurons, allowing M4R suppression of D1R signaling through AC (Jeon et al., 2010; Sánchez et al., 2009; herein incorporated by reference in their entireties). Nevertheless, the role of M4Rs in regulating synaptic plasticity in dSPNs has not been determined.

One of the unmet clinical needs for PD patients is a strategy for reducing levodopa-induced dyskinesia (LID). Levodopa (L-DOPA) treatment is a mainstay for early and mid-stage PD patients. Although it is initially effective in alleviating symptoms, as the disease progresses, L-DOPA becomes less effective and the dose required to achieve symptomatic benefit rises. In most patients, high doses of L-DOPA produce unwanted dyskinetic movements. Many lines of evidence suggest that aberrant D1R-dependent synaptic plasticity is a major factor (Cenci and Konradi, 2010; Feyder et al., 2011; Heiman et al., 2014; Jenner, 2008; Picconi et al., 2003; herein incorporated by reference in their entireties). In particular, it is thought that repeated L-DOPA treatment heightens D1R signaling, leading to pathological LTP of corticostriatal synapses and inappropriately timed or scaled dSPN activity (Picconi et al., 2003; herein incorporated by reference in its entirety). Antagonizing D1Rs is not a viable therapeutic strategy because it diminishes the symptomatic benefit of L-DOPA treatment. Hence, identifying an alternative means of normalizing D1R signaling would provide relief from LID.

SUMMARY

Provided herein are compositions and methods for the treatment and prevention of levodopa-induced dyskinesias (LID). In particular, M4 muscarinic receptor (M4R) positive allosteric modulators (PAMs) are administered to reduce dyskinetic behavior.

In some embodiments, provided herein are methods of treating a psychomotor disease comprising co-administering levodopa and a 4 muscarinic receptor (M4R) positive allosteric modulator (PAM) to a subject. In some embodiments, the psychomotor disease is Parkinson's disease (PD). In some embodiments, the levodopa and M4R-PAM are administered simultaneously. In some embodiments, the levodopa and M4R-PAM are co-formulated. In some embodiments, the levodopa and M4R-PAM are administered sequentially and in separate pharmaceutical formulations. In some embodiments, the M4R-PAM is a small molecule. In some embodiments, the M4R-PAM is selected from the group consisting of VU0467154, VU010010, and VU152100 (See, FIG. 11).

In some embodiments, provided herein are methods of treating levodopa-induced dyskinesias (LID) in a subject being treated with levodopa comprising administering an M4R PAM. In some embodiments, the psychomotor disease is Parkinson's disease (PD). In some embodiments, the levodopa and M4R-PAM are administered simultaneously. In some embodiments, the levodopa and M4R-PAM are co-formulated. In some embodiments, the levodopa and M4R-PAM are administered sequentially and in separate pharmaceutical formulations. In some embodiments, the M4R-PAM is a small molecule. In some embodiments, the M4R-PAM is selected from the group consisting of VU0467154, VU010010, and VU152100 (See, FIG. 11).

In some embodiments, provided herein are pharmaceutical compositions comprising levodopa and an M4R PAM. In some embodiments, the M4R-PAM is a small molecule. In some embodiments, the M4R-PAM is selected from the group consisting of VU0467154, VU010010, and VU152100 (See, FIG. 11).

In some embodiments, provided herein is the use of an M4R-PAM to treat a levodopa-induced dyskinesias in a subject. In some embodiments, the M4R-PAM is a small molecule. In some embodiments, the M4R-PAM is selected from the group consisting of VU0467154, VU010010, and VU152100 (See, FIG. 11). In some embodiments, the subject suffers from Parkinson's disease.

In some embodiments, provided herein is the use of an M4R-PAM and levodopa to treat a psychomotor disease in a subject. In some embodiments, the M4R-PAM is a small molecule. In some embodiments, the M4R-PAM is selected from the group consisting of VU0467154, VU010010, and VU152100 (See, FIG. 11). In some embodiments, the subject suffers from Parkinson's disease.

BRIEF DESCRIPTION OF THE DRAWINGS

FIG. 1A-F. M4R signaling promotes induction of LTD at dSPN glutamatergic synapses. (A) The experimental configuration. (B) The post-pre theta-burst pairing protocol for induction of LTD. (C) LTD was not induced by a post-pre timing pairing in dSPNs. Plots show EPSP amplitude and membrane input resistance as a function of time. The dashed line indicates the average EPSP amplitude before induction. The induction was performed 20 times at the vertical bar. Filled symbols specify the averages of 12 trials (±SEM). The averaged EPSP traces before and after induction are shown at the top. Scale bars, 2 mV×80 ms. (D) In the presence of D1R antagonist SCH23390 (3 μM), a post-pre timing pairing revealed LTD; the LTD was disrupted by addition of the selective M4R antagonist MT3 (100 nM). Data are represented as mean±SEM. Plot of the average EPSP amplitudes as a function of time. (E) LTD was induced by a post-pre timing pairing in the presence of the M4R PAM VU10010 (5 μM) (See, FIG. 11A). Plots show EPSP amplitude and membrane input resistance as a function of time. The induction was performed 60 times at the vertical bar. Scale bars, 4 mV×60 ms. (F)

FIG. 2A-F. Elevating endogenous ChI activity with DREADD hM3D(q) enhances LTD induction. (A) ChAT Cre-dependent expression of DREADD hM3D(q) in ChIs (mCitrine reporter) in DltdTomato BAC mouse. (B) DREADD cognate ligand CNO (10 μM) increased ChI spontaneous discharge rate recorded in cell-attached patches. (C) Box plot summary of the increase of discharge rate of ChIs. Box plot boxes indicate upper and lower quartiles; whiskers specify upper and lower 90%. (D) Schematic drawing shows the LTD recording configuration in the elevated extracellular ACh levels with bath perfusion of CNO. (E and F) Increasing local cholinergic signaling promotes induction of LTD in neighboring dSPN glutamatergic synapses. The LTD was blunted by the M4R antagonist MT3 (100 nM) or the CB 1R antagonist AM251 (2 μM). Plot of the average EPSP amplitudes as a function of time. Error bars indicate SEM.

FIG. 3A-F. M4R activation on dSPNs inhibits postsynaptic NMDAR-mediated $Ca^{2+}$ transients and currents. (A) Low (left) and high (right) magnification maximum-intensity projections of a dSPN filled with Alexa Fluor 568. Spine was stimulated with 1 ms uncaging pulse of 720-725 nm light. (B) In the presence of the D1R agonist SKF81379 (3 μM), average NMDAR $Ca^{2+}$ transients in a distal dSPN spine induced by a single glutamate uncaging pulse were reduced by the M4R PAM VU10010 (5 μM). Solid lines are averages across multiple spines and the shaded areas represent the mean±SEM. (C) Box plot summary of modulation of NMDAR-mediated $Ca^{2+}$ transients. (D) Addition of VU 10010 (5 μM) suppressed NMDAR-mediated uEPSC currents triggered by uncaging pulses of 500 Hz to five distal spines. Solid lines are averages across multiple spines and the shaded areas represent the mean±SEM. (E) NMDAR-mediated EPSCs recorded from dSPNs in the presence of muscarine (3 μM; upper traces) and muscarine+VU10010 (5 μM; lower traces). EPSCs are averages of 10 consecutive trials. (F) Left: time course of EPSC amplitude from the experiment shown in (E). Muscarine and VU10010 were applied during the time indicated by the horizontal bars. Right: box plot sum of M4R mediated modulation of NMDAR currents. All box plot boxes indicate upper and lower quartiles; whiskers specify upper and lower 90%.

FIG. 5A-F. M4R PAM rectifies dyskinesia-induced synaptic plasticity deficits in dSPNs. (A) Light microscopic image of a coronal section illustrating the loss of immunoreactivity for tyrosine hydroxylase (TH) after unilateral MFB 6-OHDA lesioning. CPu, caudate-putamen. (B) LTP induction was lost in prolonged 6-OHDA-lesioned animals. Shortly after the last injection of L-DOPA, LTP was recovered in dSPNs. Plot of average EPSP amplitude as a function of time. (C) The LTP was disrupted by U0126 (10 μM) or VU10010 (5 μM). Solid line (average) and shadow (±SEM) are LTP from the panel (B) for reference. (D) Low (left) and high (right) magnification maximum-intensity projections of a dSPN filled with Alexa Fluor 568. (E) NMDAR-mediated $Ca^{2+}$ transients were decreased by addition of VU10010 (5 μM) in dSPNs from LID mice. Solid lines are averages across multiple spines and the shaded areas represent the mean±SEM. (F) In dyskinetic animals, synaptic depotentiation was lost and restored by bath application of SCH23390 (3 μM) or VU10010 (5 μM). Horizontal bar indicates LFS (2

Hz, 10 min). Error bars represent SEM. Box plot boxes specify upper and lower quartiles; whiskers indicate upper and lower 90%.

FIG. 6A-E. M4R PAM alleviates dyskinetic AIMs. (A) Plot of sum of AIM scores as a function of time. Systemic treatment of VU152100 (60 mg/kg) (See, FIG. 11B) treatment significantly reduced cumulative AIM scores. (B) Box plot summation shows a dose-dependent effect of VU152100. Three doses (20, 60, 120 mg/kg) are used as indicated by horizontal bars. (C) Application of VU152100 reduced expression of phosphorylated ERK signaling molecules, phosphor-ERK (pERK) and phosphor-histone3 (pH3), in the dorsolateral striatum. (D) Sum of expression of pERK and pH3 expressed neurons in L-DOPA or L-DOPA and VU152100 treated animal group. (E) Proposed signaling model of L-DOPA-induced synaptic plasticity deficits and dyskinesia in dSPNs. Box plot boxes indicate upper and lower quartiles; whiskers specify upper and lower 90%.

FIG. 7A-D. M4R Regulates dSPN LTD through RGS4 Signaling. (A) LTD was induced with fewer (20) repetitions of the post-pre pairing protocol by co-application of the ACh esterase inhibitor physostigmine (PHY; 10 µM) and VU10010 (VU; 5 µM). The induction was blunted in the presence of the M4R antagonist MT3 (100 nM). Plot of normalized EPSP amplitude as a function of time. The dashed line represents the average of EPSP amplitude before induction. STDP induction is indicated by the vertical bar. (B) Intracellular application of the RGS4 specific inhibitor CCG203769 (CCG; 10 µM) promoted the induction of LTD, even in the absence of the M4R PAM VU10010. The LTD was disrupted by the mGluR5 antagonist MPEP (10 µM). (C) CCG enhanced LTD induction even in the presence of M4R antagonist. Solid line (average) and gray shadow (±SEM) are the LTD antagonism by MT3 from (A) for reference. Plot of the average EPSP amplitudes as a function of time is shown. Error bars indicate SEM. (D) Schematic showing the proposed signaling pathway through which M4Rs and D1Rs modulate the induction of dSPN LTD; AEA, anandamide.

Figure 8A:
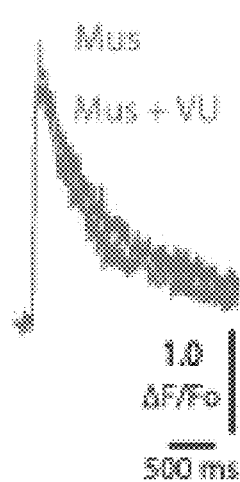
Figure 8B:
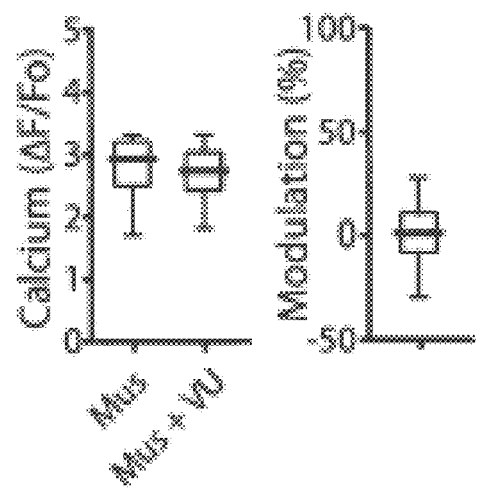

FIG. 8A-B. M4R PAM does not alter NMDAR mediated $Ca^{2+}$ transient in resting condition. (A) Average NMDAR $Ca^{2+}$ transients in distal dSPN spine induced by a single glutamate uncaging pulse were not changed by the M4R PAM VU10010 (5 µM; n=10; p>0.05, Wilcoxon test). Solid lines are means of multiple spines and the shaded areas represent the mean ±SEM. (B) Box plot summary of a group of 10 spines. Box plot boxes specify upper and lower quartiles; whiskers indicate upper and lower 90%.

Figure 9:
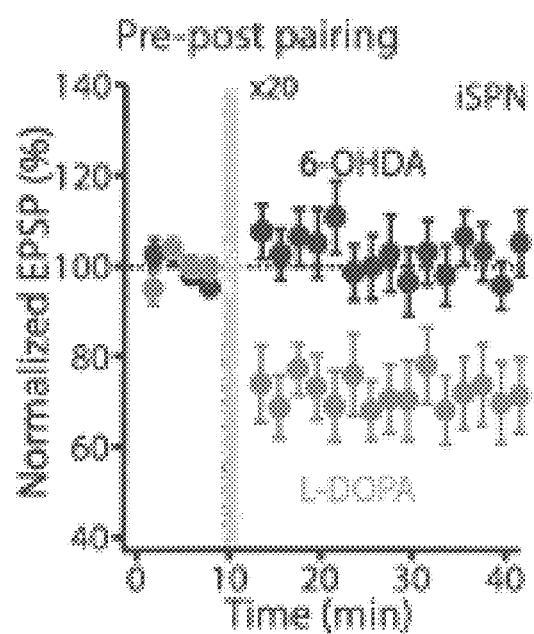

FIG. 9. L-DOPA treatment promotes induction of LTD at iSPN synapses. LTP was not induced with the pre-post pairing protocol in iSPNs from 6-OHDA lesioned animals (n=5; p>0.05, Wilcoxon test). Plot of normalized EPSP amplitude as a function of time. The dashed line shows the average of EPSP amplitude before induction. The induction was performed 20 times at the vertical bar. Shortly after L-DOPA treatment, the pre-post pairing protocol induced an LTD in iSPNs (6-OHDA n=5; L-DOPA n=5; p<0.05, Mann-Whitney test).

Figure 10A:
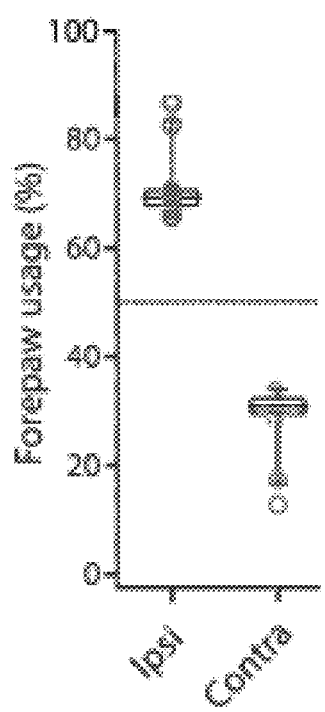
Figure 10B:
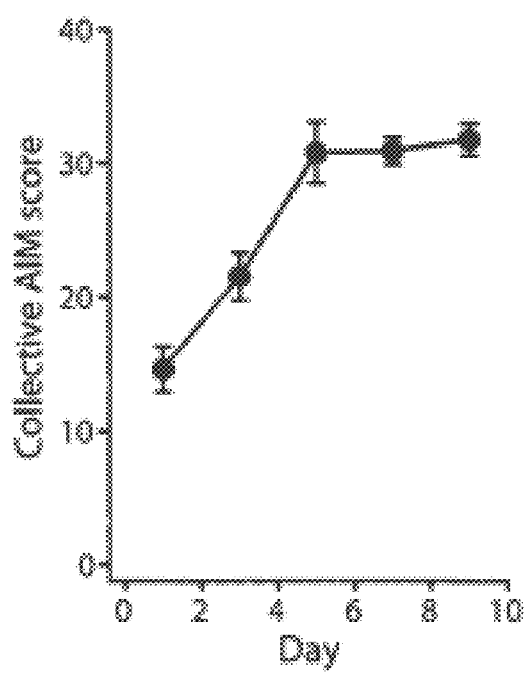

FIG. 10A-B. Forelimb-use asymmetry test (cylinder test) and AIM scoring. (A) The percentages of use of the ipsilateral (non-impaired) and contralateral (impaired) forelimbs relative to the total number of limb-use movements. (B) Cumulative axial, limb and orolingual AIM scores as a function of time. Data were from a group of 12 mice. Error bars are SEM.

Figure 11A:
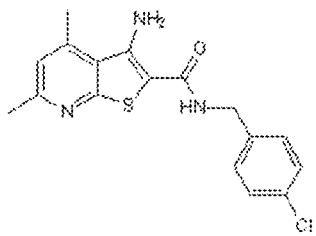
Figure 11B:
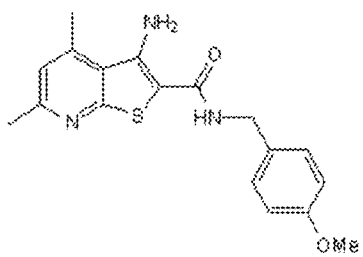
Figure 11C:
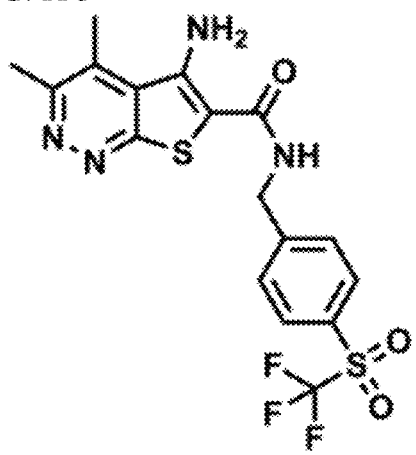

FIG. 11A-C shows chemical structures of exemplary MR4 PAMs.

Figure 12:
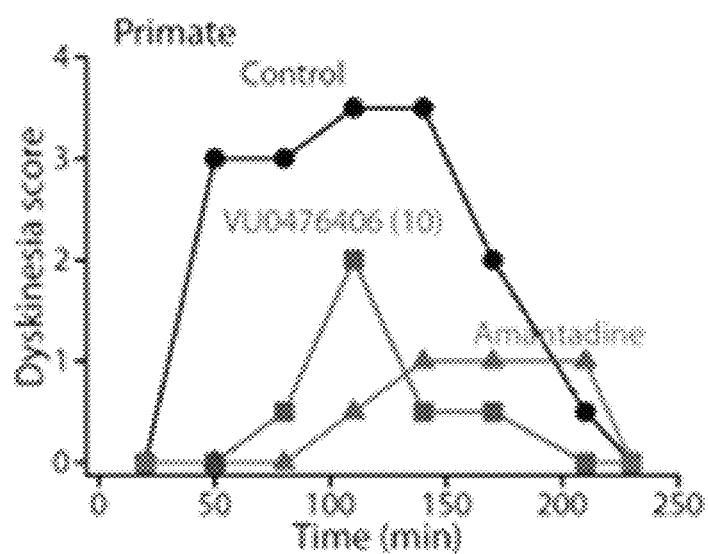

FIG. 12. Plot of sum of primate dyskinesia scores (median) as a function of time (Fr=11.64, n=4; p<0.01, Friedman's test).

Figure 13:
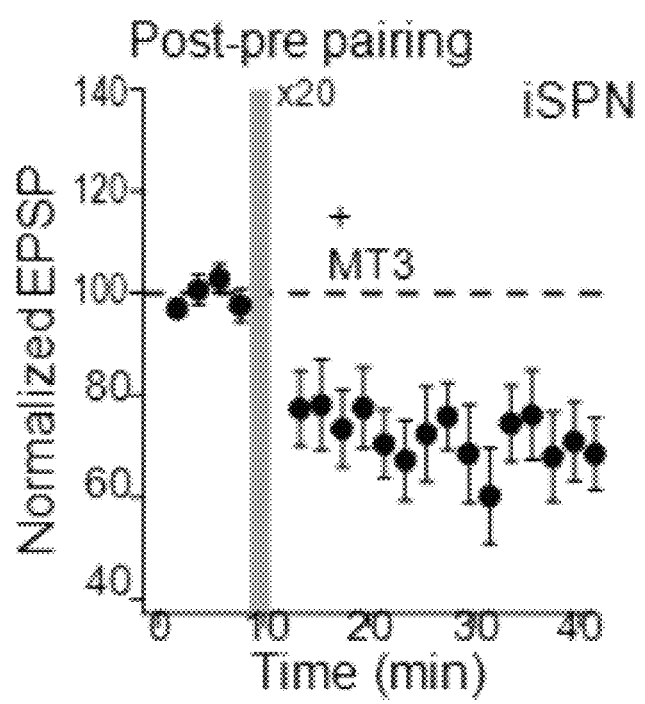

FIG. 13. Antagonism of M4R signaling does not alter iSPN LTD induction. LTD was induced with the post-pre pairing protocol in iSPNs in the presence of the M4R antagonist MT3 (100 nM; n=6; p<0.05, Wilcoxon test). Plot of normalized EPSP amplitude as a function of time. Data are represented as mean±SEM. The dashed line represents the average of EPSP amplitude before induction. STDP pairing is indicated by the vertical bar.

Figure 14:
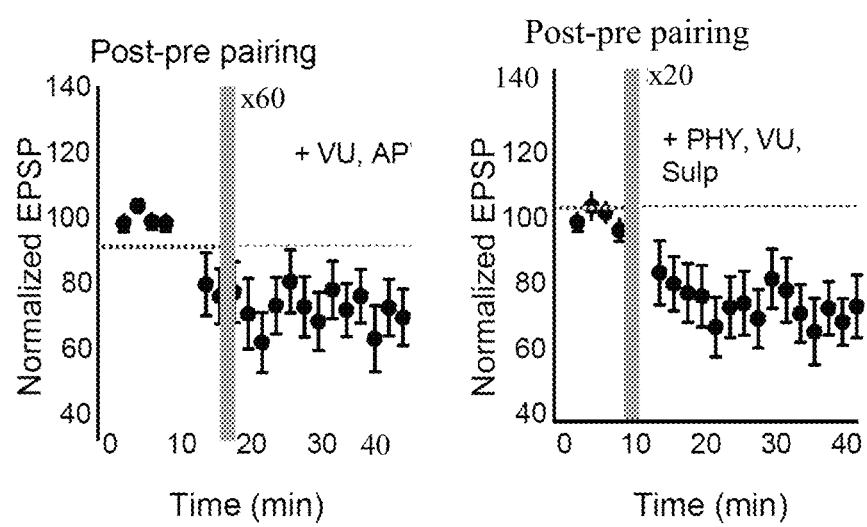

FIG. 14. NMDAR and D2R signaling are not necessary for the induction of dSPN LTD. (A) LTD was inducible with the post-pre pairing protocol by application of VU10010 (VU; 5 µM) and APV (50 µM) (n=6; p<0.05, Wilcoxon test). Plot of normalized EPSP amplitude as a function of time. Data are represented as mean±SEM. The dashed line represents the average of EPSP amplitude before induction. The vertical bar indicates STDP pairing. (B) LTD was induced with the post-pre pairing protocol in dSPNs when the D2R antagonist sulpiride (Sulp; 10 µM) was applied, together with physostigmine (Phy; 10 µM) and VU (5 µM) (n=6; p<0.05, Wilcoxon test). Plot of normalized EPSP amplitude as a function of time. Data are shown as mean±SEM.

Figure 15A:
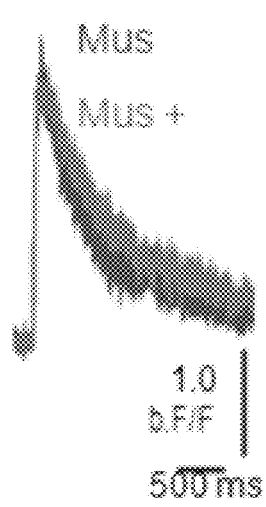
Figure 15B:
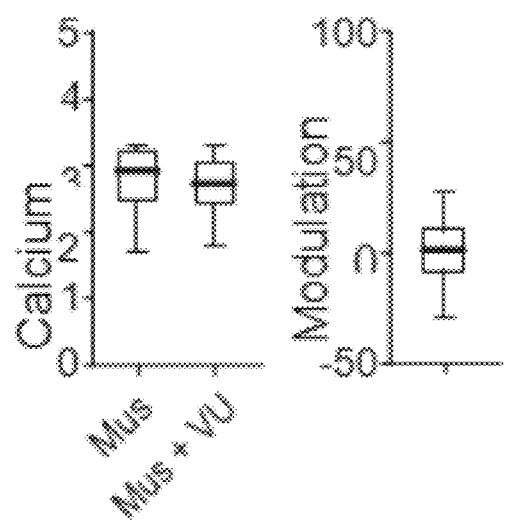

FIG. 15A-B. M4R PAM does not alter NMDAR mediated $Ca^{2+}$ transient in resting condition. (A) Average NMDAR $Ca^{2+}$ transients in distal dSPN spine induced by a single glutamate uncaging pulse were not changed by the M4R PAM VU10010 (5 µM; n=10; p>0.05, Wilcoxon test). Solid lines are means of multiple spines and the shaded areas represent the mean ±SEM. (B) Box plot summary of a group of 10 spines. Box plot boxes specify upper and lower quartiles; whiskers indicate upper and lower 90%. Mus, muscarine.

Figure 16:
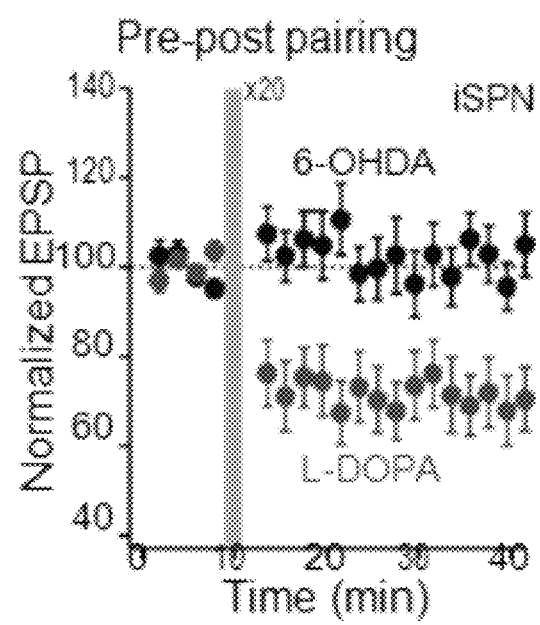

FIG. 16. L-DOPA treatment promotes induction of LTD at iSPN synapses. LTP was not induced with the pre-post pairing protocol in iSPNs from 6-OHDA lesioned animals (n=5; p >0.05, Wilcoxon test). Plot of normalized EPSP amplitude as a function of time. Data are shown as mean±SEM. The dashed line represents the average of EPSP amplitude before induction. The vertical bar indicates STDP induction. Shortly after L-DOPA treatment, the pre-post pairing protocol induced an LTD in iSPNs (6-OHDA n=5; L-DOPA n=6; p<0.05, Mann-Whitney test).

FIG. 17A-B. M4R PAM diminishes number of striatal biomarkers associated with LID. (A) Application of the M4R PAM VU0152100 (60 mg kg-1) reduced the levels of LID biomarkers, phosphorylated ERK (pERK) and phosphorylated histone3 (pH3), in the dorsolateral striatum. (B) Number of pERK- and pH3-positive neurons in L-DOPA or L-DOPA and VU0152100 treated animal groups. Box plot boxes specify upper and lower quartiles; whiskers indicate upper and lower 90%.

Figure 18:
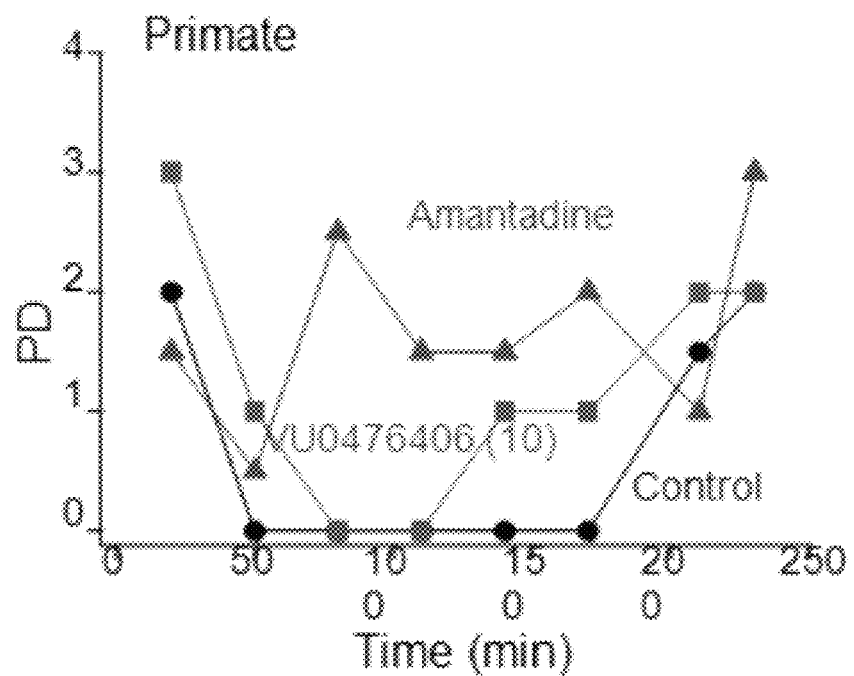

FIG. 18. M4R PAM does not compromise anti-parkinsonian effect of L-DOPA. The reduction in primate dyskinetic scores by VU0476406 did not occur at the expense of anti-parkinsonian effect of L-DOPA on PD disability (n=4; p>0.05, Friedman's test and Dunn's test). Data are represented as median.

FIG. 19A-B. Forelimb-use asymmetry test (cylinder test) and AIM scoring. (A) The percentages of use of the ipsilateral (ipsi; non-impaired) and contralateral (contra; impaired) forelimbs relative to the total number of limb-use movements. Box plot boxes indicate upper and lower quartiles; whiskers specify upper and lower 90%. (B) Cumulative axial, limb and orolingual AIM scores as a function of time. Data were from a group of 12 mice. Error bars are SEM.

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an M4R-PAM" is a reference to one or more M4R-PAMs and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., an MR4-PAM, levodopa, and/or additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are compositions and methods for the treatment and prevention of levodopa-induced dyskinesias (LID). In particular, M4 muscarinic receptor (M4R) positive allosteric modulators (PAMs) are administered to reduce dyskinetic behavior.

Experiments conducted during development of embodiments described herein demonstrate that endogenous cholinergic signaling through M4Rs promotes long-term depression of corticostriatal glutamatergic synapses and blocks D1 dopamine receptor (D1R) dependent long-term potentiation (LTP) in dSPNs. M4R signaling was examined in a mouse model of Parkinson's disease in which repeated administration of L-3,4-dihydroxyphenylalanine (L-DOPA) had induced dyskinesia attributable to an enhancement of D1R-dependent LTP in dSPNs. Boosting M4R signaling with a positive allosteric modulator (PAM) blocked aberrant LTP in dSPNs, enabled reversal of established LTP, and attenuated dyskinetic behaviors. These studies identify an important signaling pathway controlling striatal synaptic plasticity and provide a pharmacological strategy for alleviating dyskinesia in PD patients.

Experiments conducted during development of embodiments described herein demonstrate: (1) endogenous cholinergic signaling through M4Rs promotes the induction of LTD at dSPN glutamatergic synapses; in this respect, dSPN M4Rs serve a role that is analogous to that of iSPN D2Rs; (2) enhancing endogenous M4R signaling with an M4R PAM mitigates the synaptic plasticity deficits in dSPNs accompanying L-DOPA treatment; and (3) systemic treatment with the M4R PAM ameliorates LID in a mouse model. These findings not only provide a new insight into the way in which DA and ACh interact to shape striatal plasticity, they provide a therapy for one of the major unmet medical needs for PD patients—a pharmacological strategy for alleviating LID.

Prior to the experiments conducted during development of embodiments described herein, the question of how corticostriatal glutamatergic LTD is controlled in dSPNs in physiologically relevant situations was unresolved. In iSPNs, the landscape is well defined. D2Rs, mGluR5s and L-type calcium channels are necessary participants in the postsynaptic generation of eCBs that act at presynaptic glutamatergic terminals to bring about a sustained reduction in glutamate release. This is true in iSPNs, regardless of whether a spike-timing-dependent plasticity (STDP) or high-frequency stimulation (HFS) protocol is used. With HFS protocols utilizing macroelectrodes that directly stimulate the striatum, D2R signaling is also necessary for LTD induction in dSPNs. But, this dependence is indirect, reflecting the need to suppress ACh release from ChIs (Tozzi et al., 2011; Wang et al., 2006; herein incorporated by reference in their entireties).

In STDP protocols that use minimal local stimulation (MLS), D2R signaling is not necessary for LTD induction in dSPNs (Shen et al., 2008; herein incorporated by reference in its entirety). In fact, a number of studies using MLS have failed to find LTD in dSPNs (Kreitzer and Malenka, 2007; Nazzaro et al., 2012; Shen et al., 2008; herein incorporated by reference in their entireties). This has been attributed to the inadvertent stimulation of dopaminergic fibers by MLS, as antagonism of D1Rs restored LTD in dSPNs (Shen et al., 2008).

Experiments conducted during development of embodiments described herein demonstrate that activation of M4Rs, which blunt D1R stimulation of AC in dSPNs (Jeon et al., 2010; herein incorporated by reference in its entirety), enables MLS-evoked LTD induction, even in the absence of a D1R antagonist. Enhancing M4R signaling in any of three ways—by use fan M4R PAM, by slowing ACh metabolism or by increasing the activity of ChIs with a DREADD—was sufficient to establish STDP LTD. These results are consistent with M4Rs role in counteracting the behavioral activation produced by D1R agonists (Gomeza et al., 1999; Jeon et al., 2010; herein incorporated by reference in their entireties).

Even in the absence of D1R signaling, M4Rs were necessary for LTD induction in dSPNs, much like D2Rs in iSPNs.

Although the predominant expression site of striatal M4Rs is dSPNs, they are positioned at other sites in the striatum where they are poised to exert concerted effects. For example, M4Rs on corticostriatal glutamatergic terminals reduce the number of released vesicles (Higley et al., 2009; Pancani et al., 2014). M4Rs also are found on ChIs, where they act as autoreceptors (Bonsi et al., 2008; Ding et al., 2010; herein incorporated by reference in their entireties). By limiting the duration of ACh release, M4R autoreceptors diminish activation of nicotinic receptors on nigrostriatal axons and DA release (Threlfell et al., 2010; herein incorporated by reference in its entirety); limiting ACh release could also reduce activation of lower affinity M1Rs (Loudon et al., 1997; herein incorporated by reference in its entirety), which increase (rather than decrease) dSPN excitability (Hernández-Flores et al., 2015; herein incorporated by reference in its entirety).

In addition to promoting the induction of LTD, M4R signaling blocked D1R-mediated LTP induction in dSPNs. LTP induction in dSPNs requires co-activation of PKA and Ras-guanine nucleotide exchange factor 1 (Ras-GEF1), which converge upon ERK (Cerovic et al., 2015; Sweatt, 2004; Zhu et al., 2002; herein incorporated by reference in their entireties). Experiments were conducted during development of embodiments described herein indicate that M4R signaling blunts activation of both PKA and Ras-GEF1. First, M4Rs are well-known to inhibit AC isoforms by activating Gi proteins (Caulfield and Birdsall, 1998; herein incorporated by reference in its entirety); blunting the elevation in cytosolic cAMP subsequent to D1R stimulation, limiting PKA activation (Gomeza et al., 1999; Hervé, 2011; Jeon et al., 2010; herein incorporated by reference in their entireties). Second, M4Rs reversed D1R-mediated enhancement of NMDAR $Ca^{2+}$ currents, which is brought about by phosphorylation of serine 1166 on GluN2B (Murphy et al., 2014; herein incorporated by reference in its entirety). This reversal should blunt activation of the $Ca^{2+}$/calmodulin dependent Ras-GEF1 anchored to the GluN2B subunit (Krapivinsky et al., 2003; herein incorporated by reference in its entirety). The strength of dSPN glutamatergic synapses is bidirectionally modulated by M4Rs and D1Rs.

M4R signaling promotes LTP reversal or depotentiation in dSPNs. LTP at SPN glutamatergic synapses is postsynaptically expressed, resulting from AMPA trafficking into the synapse (Plotkin et al., 2014; herein incorporated by reference in its entirety). The ability of M4Rs to depotentiate synapses is attributable to inhibition of AC and diminishes PKA phosphorylation of DARPP-32, resulting in dis-inhibition of PP1 and removal of AMPARs that have been recently trafficked into the synapse (Lee et al., 2000; Otmakhova and Lisman, 1998; Picconi et al., 2003; Zhuo et al., 1999; herein incorporated by reference in their entireties).

In experiments conducted during development of embodiments described herein, tissue was taken from LID mice shortly after the last L-DOPA dose, STDP LTP was readily induced in dSPNs and did not de-potentiate with LFS. Depotentiation was immediately restored by D1R antagonism or M4R agonism, which is not basically different from the situation in tissue from naïve mice. Moreover, LTP induction was blocked by addition of the M4R PAM, much as in naïve tissue. However, in L-DOPA treated mice, rather than being briefly stimulated by burst spiking of DA neurons, D1Rs in the LID model are stimulated for long periods of time, giving the appearance of apparent receptor supersensitivity. The sustained elevation of extracellular DA following L-DOPA administration also prevents iSPNs from responding to patterned activity appropriately. In this state, STDP protocols that normally induce Hebbian LTP, induce LTD. This cell-specific biasing of synaptic plasticity—LTP for dSPNs and LTD for iSPNs—in the LID models is consistent with the hyperkinetic features of LID. However, the strength of SPN synapses should be unconstrained by action outcomes, leading to random alterations in strength. It is contemplated that this randomness is responsible for lack of purposeful involuntary movement during bouts of dyskinesia.

Antagonizing D1Rs is not a viable therapeutic strategy for ameliorating the aberrant plasticity in dSPNs because it would diminish the symptomatic benefit of L-DOPA treatment. By amplifying endogenous cholinergic signaling, the M4R-PAMs disrupted STDP LTP in dSPNs and enabled previously potentiated synapses to be depotentiated. In addition, they diminished NMDAR-mediated $Ca^{2+}$ signaling and phosphorylation of ERK in dyskinetic mice—a biomarker of the dyskinetic state (Pavón et al., 2006; Santini et al., 2007; Westin et al., 2007; herein incorporated by reference in their entireties). Systemic administration of an M4R-PAM significantly diminished dyskinetic behavior in mice following L-DOPA treatment. This was accomplished without compromising the symptomatic benefit of L-DOPA treatment.

M4Rs expressed by dSPNs play a central role in the regulation of synaptic plasticity of glutamatergic synapses in both healthy and parkinsonian states. These receptors promoted LTD and blocked LTP induction; they also enabled depotentiation. In parkinsonian mice rendered dyskinetic by L-DOPA treatment, an M4R-PAM blunted D1R-mediated LTP and enabled depotentiation; the dyskinetic behaviors were attenuated by systemic M4R-PAM treatment as well.

In some embodiments, provided herein are method of treating levodopa-induced dyskinesias (LID) (e.g., induced during treatment of, for example, Parkinson's disease) comprising administering an M4R-PAM to a subject. In some embodiments, an M4R-PAM and levodopa are co-administered. Exemplary M4R-PAMs for the treatment or prevention of LID include, VU10010, VU152100, and VU0467154 (FIG. 11). Other exemplary M4R-PAMs for the treatment or prevention of LID include the compounds and other agent described in, for example: U.S. Pub No. 20130178458; U.S. Pub No. 20140194471; U.S. Pat. Nos. 9,029,563; 8,697,888; 8,772,509; U.S. Pub No. 20130158078; U.S. Pub No. 20130261107; U.S. Pub No. 20140057870; U.S. Pub No. 20160102090; U.S. Pub No. 20150361081; U.S. Pub No. 20160096833; U.S. Pat. Nos. 9,192,603; 9,090,632; U.S. Pub No. 20130079366; U.S. Pub No. 20140364409; U.S. Pat. Nos. 8,592,422; 8,431,700; 9,056,875; 8,497,289; 8,916,584; U.S. Pub No. 20130065895; U.S. Pub No. 20140213593; U.S. Pub No. 20130096110; U.S. Pub No. 20130345205; U.S. Pat. Nos. 8,710,074; 8,658,650; 9,255,103; 9,163,015; 8,703,946; 9,108,963; U.S. Pub No. 20130040944; U.S. Pub No. 20130338154; U.S. Pub No. 20130123236; U.S. Pub No. 20140206676; U.S. Pat. Nos. 7,531,541; 9,180,192; 8,211,933; U.S. Pub No. 20130252943; U.S. Pub No. 20130345204; U.S. Pub No. 20140329838; U.S. Pat. Nos. 8,969,389; 9,073,935; 9,012,445; U.S. Pub No. 20150018309; U.S. Pub No. 20140357615; U.S. Pub No. 20110124663; U.S. Pub No. 20140288084; U.S. Pub No. 20140206707; U.S. Pat. No. 8,865,725; U.S. Pub No. 20130345206; U.S. Pat. Nos. 9,056,876; 8,759,377; 8,501,757; 8,796,295; 8,569,308; 8,598,345; 9,085,562; 8,901,125; 8,034,806; 8,853,392; 8,697,691; U.S. Pub No. 20150266866; U.S. Pub No. 20120245185; U.S. Pat. Nos. 8,207,155; 8,436,019; 8,912,336; U.S. Pub No. 20120245153; U.S. Pub No. 20130345203; U.S. Pub No. 20150216863; U.S. Pat. Nos. 8,853,237; 9,029,366; 8,779,157; incorporated by reference in their entireties.

In some embodiments, provided herein are pharmaceutical compositions comprising a therapeutic agent (e.g., M4R-PAM, etc.), alone or in combination with at least one other non-therapeutic agent, such as a stabilizing compound, and may be administered in any sterile, biocompatible pharmaceutical carrier, including, but not limited to, saline, buffered saline, dextrose, and water.

As is well known in the medical arts, dosages for any one patient depends upon many factors, including the patient's size, body surface area, age, the particular compound to be administered, sex, time and route of administration, general health, and interaction with other drugs being concurrently administered.

Pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, pharmaceutical compositions may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions are formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions include compositions wherein the active ingredients (e.g., M4R-PAM, etc.) are contained in an effective amount to achieve the intended purpose. For example, an effective amount of therapeutic may be that amount that prevents levodopa-induced dyskinesias and/or treats or reduced symptoms associated with PD. Determination of effective amounts is well within the capability of those skilled in the art, especially in light of the disclosure provided herein.

In addition to the active therapeutic ingredients, pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions. The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (e.g., dosage).

Pharmaceutical preparations for oral administration include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Therapeutic compositions formulated in a pharmaceutical acceptable carrier may be prepared, placed in an appropriate container, and labeled for treatment of the indicated condition (e.g., levodopa-induced dyskinesias, PD, etc.).

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

In some embodiments, a therapeutically effective dose may be estimated initially from cell culture assays and/or animal models (particularly murine models). A therapeutically effective dose refers to that amount that effectively addresses and underlying cause and/or ameliorates symptoms of the disease state or unwanted condition (e.g., levodopa-induced dyskinesias, PD, etc.). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. Data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration. The exact dosage is chosen by the individual clinician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination (s), reaction sensitivities, and tolerance/response to therapy. Long acting pharmaceutical compositions might be administered every 3 to 4 days, every week, or once every two weeks depending on half-life and clearance rate of the particular formulation.

Typical dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; 5,225,212; WO2004/097009, or WO2005/075465, each of which are herein incorporated by reference).

In some embodiments, the therapies disclosed herein are combined or used in combination with other agents useful in the treatment of psychomotor diseases (e.g., PD). Or, by way of example only, the therapeutic effectiveness of one of the therapies described herein may be enhanced by administration of an adjuvant (e.g., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In some embodiments, one or more of the therapies provided herein (e.g., M4R-PAM, levodopa, etc.) are combined with each other, and/or with one or more treatments for a psychomotor disease (e.g., PD). Suitable treatments for psychomotor disease (e.g., PD) for co-administration (e.g., with M4R-PAM, levodopa, etc.) include dopamine agonists (e.g., bromocriptine, pergolide, pramipexole, ropinirole, piribedil, cabergoline, apomorphine, lisuride, etc.), MAO-B inhibitors (e.g., selegiline, rasagiline, etc.), and other therapeutics, such as amantadine, anticholinergics, quetiapine, cholinesterase inhibitors, modafinil, non-steroidal anti-inflammatory drugs, etc.

In some embodiments, one or more therapeutic approaches described herein co-administered to a subject.

In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition.

The technology provided herein also includes kits for use in the instant methods. Kits of the technology comprise one or more containers comprising a therapeutic approach described herein and/or a second agent, and in some variations further comprise instructions for use in accordance with any of the methods provided herein. The kit may further comprise a description of selecting an individual suitable treatment. Instructions supplied in the kits of the technology are typically written instructions on a label or package insert (e.g., a paper insert included with the kit), but machine-readable instructions (e.g., instructions carried on a magnetic or optical storage disk) are also contemplated. In some embodiments, the kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag, or a syringe. The containers can optionally include indicia indicating that the containers have been autoclaved or otherwise subjected to sterilization techniques. The kit can include instructions for administering the various solutions contained in the containers to subjects.

EXPERIMENTAL

Example 1

Materials and Methods

Animals

Male C57Bl/6 and FVB mice expressing tdTomato or eGFP under control of either the Drd1 or Drd2 receptor regulatory elements were used. All the mice used for the study were hemizygous for these transgenes. For some experiments, D1-tdTomato BAC mice were crossed with a transgenic line expressing Cre recombinase under control of the ChAT promoter. All mice were 8-10 weeks of age before stereotaxic surgery. Animal use procedures were reviewed and approved by the Northwestern Institutional Animal Care and Use Committee.

Slice Preparation and Electrophysiology

Mice were deeply anesthetized intraperitoneally with a mixture of ketamine (50 mg kg−1) and xylazine (4 mg kg−1) and perfused transcardially with 5-10 ml of ice-cold artificial CSF (aCSF) comprising (in mM): 125 NaCl, 2.5 KCl, 1.25 $NaH_2PO_4$, 2.0 $CaCl_2$, 1.0 $MgCl_2$, 26 $NaHCO_3$ and 10 glucose (305 mOsm $l^{-1}$). Parasagittal corticostriatal slices (250 μm) were cut in ice-cold external solution containing (mM) 110 choline chloride, 26 $NaHCO_3$, 1.25 $NaH_2PO_4$, 2.5 KCl, 0.5 $CaCl_2$, 7 $MgCl_2$, 11.6 sodium ascorbate, 3.1 sodium pyruvate and 5 glucose (305 mOsm $l^{-1}$). Slices were then transferred to a holding chamber containing aCSF. After an incubation period at 34° C. for 30 min, the slices were then kept in the holding chamber at the room temperature for another 30 min before use.

Individual slices were transferred to a recording chamber and were continuously perfused (2-3 ml min$^{-1}$) with aCSF for the duration of the experiment. Experiments were performed in the dorsolateral striatum at elevated temperature (30-31° C.).

For whole-cell voltage clamp recordings, patch pipettes were loaded with internal recording solution containing (mM): 120 $CsMeSO_3$, 15 CsCl, 8 NaCl, 10 HEPES, 0.2 EGTA, 10 tetraethylammonium Chloride (TEA-Cl), 5 QX-314, 2 Mg-ATP, 0.3 Na-GTP; pH was adjusted to 7.25 with CsOH and osmolarity to ~305 mOsm $l^{-1}$. All the recordings were made using a MultiClamp 700 A amplifier, and signals were filtered at 2 kHz and digitized at 10 kHz. Data were excluded when the series resistance changed >20% over the time course of the experiment. For perforated patch recordings, the internal recording solution comprised (in mM): 125 KMeSO4, 14 KCl, 2 $MgCl_2$, 0.2 EGTA, 10 HEPES; pH was adjusted to 7.25 with NaOH and osmolarity to ~280 mOsm $l^{-1}$. Amphotericin B was used to achieve electrical access through the perforated-patch method (Shen et al., 2007; 2008; herein incorporated by reference in their entireties). Capacitance current was continuously monitored during perforation by applying a 5-10 mV pulse from a holding potential of −70 mV. The amplifier bridge circuit was adjusted to compensate for series resistance and continuously monitored during recordings. Electrode capacitance was also compensated. Data were excluded when the input resistance (Ri) changed >20% over the time course of the experiment.

EPSPs were evoked by focal extracellular stimulation with a small theta glass electrode positioned ~100 μm from the recording electrode. Long-lasting synaptic plasticity was induced using protocols consisting of subthreshold synaptic stimulation paired with back-propagating action potentials (bAPs) at theta frequency (5 Hz). These protocols consisted of 20-60 trains of five bursts repeated at 0.1 Hz, with each burst composed of three bAPs preceded with three EPSPs at 50 Hz (positive timing, +5 ms) or three bAPs followed by one EPSP (negative timing, −10 ms). The time interval Δt was defined as the time between the onset of the EPSP and the AP closest in time to the EPSP. To ensure induction of consistent synaptic plasticity, postsynaptic neurons were depolarized to −70 mV from their typical resting membrane potentials (−85 mV) during their induction. GABAA was blocked by the bath application of gabazine (10 μM).

Unilateral 6-OHDA Model and LID

Mice were anaesthetized with an isoflurane precision vaporizer (Smiths Medical PM, Inc., Norwell, Mass.), placed in a stereotaxic frame (David Kopf Instruments, Tujunga, Calif.), and a hole was drilled over the MFB. After exposing the skull, 3.5 mg ml$^{-1}$ free base 6-OHDA hydrobromide with 0.02% ascorbic acid was injected using a calibrated glass micropipette at the following coordinates: AP: −0.7; ML: −1.2; DV: −4.75 (Shen et al., 2008; herein incorporated by reference in its entirety). Mice were monitored daily after surgery and supplemented with saline injections and high-fat/high-sucrose food if necessary. Two weeks after surgery, the degree of damage to nigrostriatal DA neurons was assessed with a forelimb-use asymmetry test (cylinder test) (Tillerson et al., 2001; herein incorporated by reference in its entirety). Forelimb use during explorative activity was video recorded in a transparent cylinder (8 cm diameter and 12 cm height) for 3 min immediately after animals were placed in the cylinder. The number of ipsilateral and contralateral (to lesioned hemisphere) forelimb weight supporting paw contacts was counted. The percentages of use of the non-impaired and impaired forelimbs relative to the total number of limb-use movements were obtained (FIG. 10A). Striatal sections from a subset of mice were stained with tyrosine hydroxylase to verify successful lesion (FIG. 5A). One day after the cylinder test, mice underwent behavioral testing for abnormal involuntary movements (AIMs) following L-DOPA treatment (Francardo et al., 2011; herein incorporated by reference in its entirety). Mice were transferred to a behavioral testing room, placed in standard housing cages and administered i.p. injections. For in vitro brain slice recording, behavioral testing occurred every other day for a total of five test sessions. Animals received 3 and 6 mg kg$^{-1}$ L-DOPA for the first two and last three behavioral sessions, respectively. Benserazide was co-administered at 12 mg kg$^{-1}$ to inhibit peripheral conversion of L-DOPA to DA. AIMs (axial, limb and orolingual movements) were rated as previously described (FIG. 10B) (Cenci and Lundblad, 2007; herein incorporated by reference in its entirety). Each animal was observed individually for 1 min every 20 min for 3 hours. Each AIM parameter was scored on a severity scale from 0 to 4: 0, absent; 1, present during less than half of the observation time; 2, present during more than half of the observation time; 3, present all the time but suppressible by sensory stimuli; 4, continuous, severe and not suppressible. Physiological experiments were performed one hour after the last L-DOPA administration. For behavioral pharmacology experiments as those shown in FIG. 6, treatment with L-DOPA was given for 8 days using an incremental dose regimen (Fasano et al., 2010; herein incorporated by reference in its entirety) at the doses of 1.5 mg/kg on days 1-3 and 3 mg/kg on days 4-8. After animals had reached stable AIM scores, they were randomly allocated to receive treatment with L-DOPA and Vehicle, or L-DOPA and VU152100, which was given at the doses of 20 mg/kg (day 6), 60 mg/kg (day 7) or 120 mg/kg (day 8).

Viral DREADD hM3D(q) Expression and Activation

To determine the importance of endogenous cholinergic signaling in regulating synaptic plasticity, the discharge rate of ChIs was elevated using a Cre-dependent DREADD (Alexander et al., 2009; Armbruster et al., 2007; Ferguson et al., 2011; Kozorovitskiy et al., 2012; herein incorporated by reference in their entireties). Briefly, bi-transgenic mice expressing tdTomato in dSPNs and Cre-recombinase under control of the choline acetyltransferase (ChAT) promoter received striatal stereotaxic injections of an adeno-associated virus (AAV; serotype 2/8) containing the hM3D(q) expression construct (the University of North Carolina Vector Core). Mice were allowed to recover for 5-6 weeks before recordings. To activate the DREADD expressing ChIs, clozapine-N-oxide (CNO) was bath applied to ex vivo brain slice preparations.

Two-photon Laser Scanning Microscopy dSPNs were identified by somatic tdTomato expression using two-photon excited fluorescence that was induced and detected using a Prairie Ultima laser scanning microscope system (Prairie Technologies). Fluorescent and bright-field images were viewed in register using a Dodt contrast detector system. Cells were patched using video microscopy with a Hitachi CCD camera and an Olympus 60×/1.0 NA lens. Green (Fluo 5F) and red (tdTomato; Alexa 568) signals were acquired using 810 nm excitation (Verdi/Mira laser). Following patch rupture the internal solution was allowed to equilibrate for 10-15 minutes before imaging. High magnification z-series of dendrite regions 50-100 µm from the soma were acquired with 0.072 µm2 pixels with 4 µs dwell time and 0.3 µm z-steps. At the end of each experiment whole cell z-series were acquired with 0.36 µm$^2$ pixels with 10 µs dwell times and 1 µm z-steps.

Ca$^{2+}$ Imaging and Two-photon Laser Uncaging dSPNs were loaded with 25 µM Alexa 568 and 300 µM Fluo 5F via the internal recording solution, containing (in mM): 120 CsMeSO$_3$, 5 NaCl, 10 TEA-Cl, 10 HEPES, 5 QX-314, 4 ATP-Mg and 0.3 GTP-Na. Green fluorescent line scan signals were acquired from dendritic spines at 6 ms per line and 512 pixels per line with 0.08 µm pixels and 10 µs pixel dwell time. The laser-scanned images were acquired with 810 nm light pulsed at 90 MHz (~250 fs pulse duration). Power attenuation was achieved with two Pockels cells electro-optic modulators (models 350-80 and 350-50, Con Optics, Danbury, Conn.). Changes in Fluo 5F fluorescence were averaged from 3 trials and measured as ΔF/Fo.

Glutamate uncaging was achieved using a Verdi/Mira (Coherent Laser Group, Santa Clara, Calif.) (Plotkin et al., 2014). 5 mM MNI-glutamate was superfused over the slice at 0.4 ml/hr using a syring pump and multi-barreled perfusion manifold (Cell MicroControls, Norfolk, Va.). The perfusion solution was (in mM): 124 NaCl, 3 KCl, 2 CaCl$_2$, 1 NaH$_2$PO$_4$, 26 HEPES and 16.66 glucose, and also contained (in µM): 3 muscarine, 10 serine, 10 NBQX and 10 gabazine, plus or minus: 3 SKF81297 and/or 5 VU10010). Glutamate was uncaged adjacent to individual spines using 1 ms pulses of 720-725 nm light typically 10-20 mW in power at the sample plane. Photolysis power was tuned via a third Pockels cell modulator (Con Optics, Danbury, Conn.) to achieve uEPSCs≤5 pA. uEPSC amplitudes were measured from averaged (3-5 repetitions) traces. All uncaging experiments were performed in 0 mM Mg$^{2+}$-containing solutions.

Data Analysis and Statistics Methods

Data analysis was conducted with Igor Pro 6 (Wavemetrics, Lake Oswego, Oreg.) and Clampfit 9 (Molecular Devices). EPSP amplitude was calculated from 50-60 sweeps immediately before the start of induction and 20-30 min after the end of induction. The change in EPSP amplitude was calculated by averaging EPSP values after the induction and normalized to the average baseline EPSP amplitude. Compiled data were expressed as mean±s.e.m. Statistical tests were performed using Excel (Microsoft, Redmond, Wash.) and SigmaStat (Systat, San Jose, Calif.). Non-parametric Mann-Whitney or Wilcoxon tests were used to assess the experiment results, using a probability threshold of 0.05.

Example 2

M4R Signaling was Necessary for LTD at dSPN Glutamatergic Synapses

To determine if M4Rs were modulating synaptic plasticity, a spike-timing-dependent plasticity (STDP) paradigm was used. SPNs were interrogated in ex vivo corticostriatal parasagittal brain slices from Drd1 or Drd2 bacterial artificial chromosome (BAC) transgenic mice in which dSPNs and iSPNs (respectively) expressed td-Tomato and enhanced green fluorescent protein (eGFP), allowing them to be reliably sampled (Chan et al., 2012; Gong et al., 2003; Shuen et al., 2008; herein incorporated by reference in their entireties). Once identified, neurons were monitored and controlled with perforated-patch recording to preserve intracellular signaling mechanisms and to allow stable, long-term monitoring of synaptic strength (FIG. 1A).

Figure 4A:
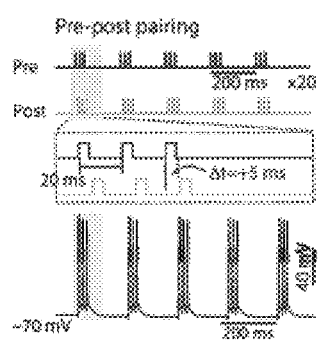
FIG. 4A-F. M4R stimulation blunts LTP induction at dSPN synapses and enables depotentiation. (A) The pre-post theta-burst pairing protocol for induction of LTP. (B) LTP was induced by a pre-post timing pairing in dSPNs. Plots show EPSP amplitude and membrane input resistance as a function of time. The dashed line indicates the average EPSP amplitude before induction. The induction was performed 20 times at the vertical bar. Filled symbols specify the averages of 12 trials (±SEM). The averaged EPSP traces before and after induction are shown at the top. Scale bars, 4 mV×80 ms. (C) LTP induction was disrupted by the mitogen-activated protein (MAP) kinase inhibitor U0126 (10 μM). Plot of the average EPSP amplitudes as a function of time. (D) LTP induction was also blocked by the M4R PAM VU10010 (5 μM). Solid line (average) and shadow (±SEM) are control LTP from the panel (C) for reference. (E) Synaptic depotentiation was not induced by LFS (@2 Hz for 10 min) during the time indicated by the horizontal bar. However, pre-perfusion of a D1R antagonist SCH23390 (3 μM) facilitated depotentiation. (F) VU10010 (5 μM) also promoted the reversal of established LTP. Solid line (average) and shadow (±SEM) are control from the panel (E) for reference. Error bars represent SEM.
Figure 4B:
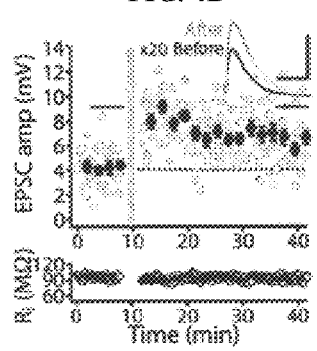

Synaptic plasticity was induced by pairing local stimulation of glutamatergic afferent fibers with postsynaptic spikes evoked by short bursts of intracellular current injection that were repeated at 5 Hz (FIGS. 1B, 4A). Pairing postsynaptic spiking with a trailing presynaptic volley failed to change EPSP amplitudes (FIG. 1C). However, the same protocol led to LTD in dSPNs when D1Rs were antagonized by bath application of the D1R antagonist SCH23390 (3 µM; n=6; p<0.05, Wilcoxon signed rank test) (FIG. 1D). The engagement of D1Rs in this experimental paradigm undoubtedly stems from the fact that local electrical stimulation activates not only glutamatergic fibers, but dopaminergic fibers as well; although the embodiments herein are not limited to any particular mechanism of action and an understanding of the mechanism of action is not necessary to practice such embodiments. Nevertheless, these results confirm that D1R signaling disrupts the induction of LTD in dSPNs (Shen et al., 2008; Wu et al., 2015; herein incorporated by reference in their entireties).

These experiments establish the ability of D1Rs to disrupt LTD induction in dSPNs. Previous work has shown that type 5 metabotropic glutamate receptors (mGluR5) are critical for STDP LTD (Fino et al., 2010; Nazzaro et al., 2012; Shen et al., 2008; herein incorporated by reference in their entireties). To test whether M4Rs play a role in dSPNs that is analogous to that of D2Rs in iSPNs (which are necessary for LTD induction (Kreitzer and Malenka, 2007; Yin and Lovinger, 2006; herein incorporated by reference in their entireties)), the selective M4R antagonist—muscarinic toxin 3 (MT3, 100 nM)—was bath applied (along with the D1R antagonist SCH23390) prior to stimulation. MT3 blocked induction of LTD (SCH23390 n=6; SCH23390+MT3 n=5; p<0.05, Mann-Whitney rank sum test) (FIG. 1D), establishing the necessity of M4R stimulation for dSPN STDP LTD, even when D1Rs were blocked.

Experiments were conducted during development of embodiments described herein to determine whether robust M4R signaling would overcome concomitant D1R signaling. To amplify appropriately timed endogenous cholinergic signaling in the STDP protocol, an M4R positive allosteric modulator (PAM) was used; PAMs do not stimulate receptors directly but enhance their response to endogenous ACh (Brady et al., 2008; Dencker et al., 2012; Shirey et al., 2008; herein incorporated by reference in their entireties). In the absence of a D1R antagonist, 20 repetitions of the pairing protocol did not lead to LTD induction in the presence of the M4R PAM VU10010 (5 µM) (n=7; p>0.05, Wilcoxon test) (FIG. 1F). This repetition number is adequate for LTD induction in iSPNs (Shen et al., 2008). However, when the number of repetitions was increased to 60 (that matched the number of presynaptic stimulation in the LTP induction protocol, see below) in the presence of the M4R PAM, LTD induction was robust in dSPNs (n=6; p<0.05, Wilcoxon test) (FIG. 1E, F). These results demonstrate that enhancing M4R signaling can lead to LTD induction even when D1Rs are activated.

Figure 7A:
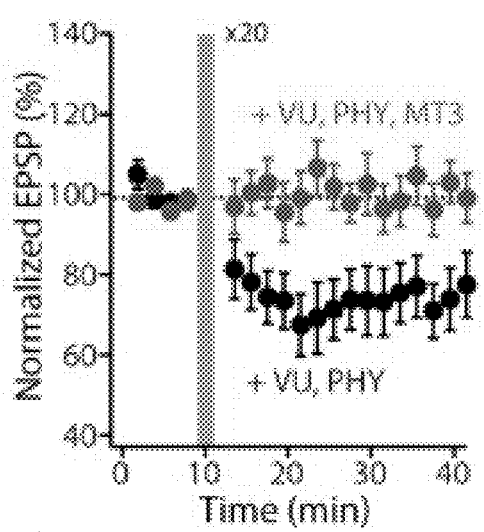

To address the possibility that in an ex vivo slice preparation at 30-31° C., spontaneous ChI activity is low and could lead to effective enzymatic degradation of ACh near its release site and weak M4R activation, the ACh esterase inhibitor physostigmine (10 µM) was co-applied with the M4R PAM. This combination led to robust LTD induction with only 20 repetitions of the pairing protocol (n=6; p<0.05, Wilcoxon test) (FIG. 7A). Another way to compensate for lower than normal cholinergic signaling in ex vivo slices is to use designer receptors exclusively activated by designer drugs (DREADDs) to selectively increase ChI discharge rate (Alexander et al., 2009; Armbruster et al., 2007; herein incorporated by reference in their entireties). To this end, bi-transgenic mice expressing tdTomato in dSPNs and Cre-recombinase under control of the choline acetyltransferase (ChAT) promoter received striatal injections of an adeno-associated virus (AAV) containing an hM3D(q) expression construct having an upstream foxed STOP codon; this STOP codon is effectively excised by Cre-recombinase leading to DREADD expression (Ferguson et al., 2011; Kozorovitskiy et al., 2012; herein incorporated by reference in their entireties) (FIG. 2A). When activated by its cognate ligand clozapine-N-oxide (CNO), the hM3D(q) receptor activates phospholipase C (PLC) signaling (Rogan and Roth, 2011; Wess et al., 2013; herein incorporated by reference in their entireties). The PLC-dependent depletion of a membrane lipid phosphotidylinositol 4,5-bisphosphate (PIP2) decreases KCNQ (Kv7) and Kir2 $K^+$ channel opening, enhancing action potential generation (Rogan and Roth, 2011; Shen et al., 2005; 2007; Wess et al., 2013; herein incorporated by reference in their entireties). In slices from these mice taken 5-6 weeks after AAV injection, bath perfusion of CNO (10 µM) increased the discharge rate of ChIs into the physiological range [control median=1.0 Hz (range: 0.7-2.0); CNO median=6.7 Hz (range: 4.2-7.8); n=5; p<0.01, Mann-Whitney test] (FIG. 2B, C). With elevated ChI activity, preceding synaptic stimulation with a short burst of postsynaptic spikes led to a robust LTD in adjacent dSPNs (n=6; p<0.05, Wilcoxon test) (FIG. 2D, E). This STDP LTD was dependent upon endocannabinoid (eCB) CB 1 receptors (AM251, 2 µM; CNO n=6; CNO+AM251 n=4; p<0.05, Mann-Whitney test) (FIG. 2E), establishing a clear mechanistic parallel to D2R-dependent LTD induced in iSPNs (Kreitzer and Malenka, 2007; Lerner and Kreitzer, 2012; Lovinger, 2010; Shen et al., 2008; Wu et al., 2015; herein incorporated by reference in their entireties).

Figure 7B:
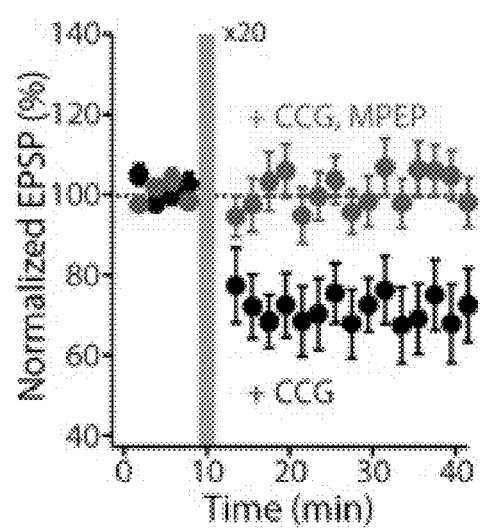
Figure 7C:
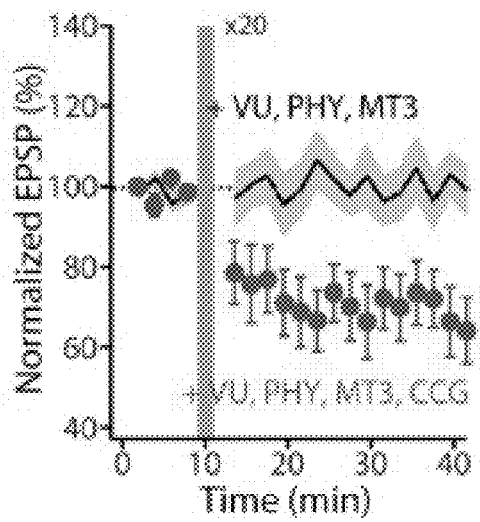
Figure 7D:
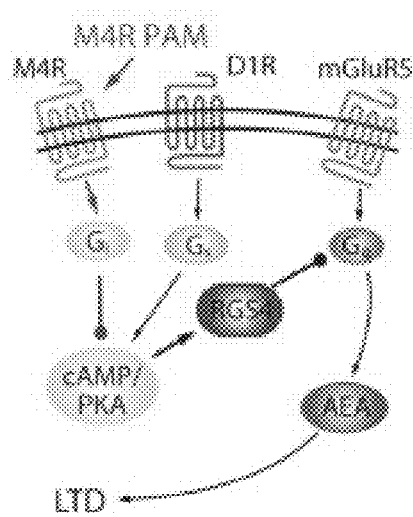

Experiments were conducted during development of embodiments herein to demonstrate that RGS4 is involved in regulation of the induction of dSPN LTD by M4Rs. A selective RGS4 antagonist CCG203769 (Blazer et al., 2015; incorporated by reference in its entirety) was used. CCG203769 was applied through the patch pipette in whole-cell mode to restrict its action to the postsynaptic neuron. Intracellular application of CCG203769 (10 µM) enhanced induction of LTD during repeated pairing of postsynaptic spikes with presynaptic stimulation 10 ms later, even without boosting M4R stimulation with VU10010. This indicates that acute inhibition of RGS4 signaling dissociates LTD induction from M4Rs (CCG203769 n=6; p<0.05, Wilcoxon test) (FIG. 7B). Indeed, when RGS4 signaling was blocked by CCG203769, antagonizing M4Rs had no effect on dSPN LTD (VU+PHY+MT3 n=6; VU+PHY+MT3+CCG203769 n=7; p<0.05, Mann-Whitney test) (FIGS. 7C and 7D). However, LTD induction still required mGluR5 stimulation, as blocking mGluR5 with MPEP (10 µM) prevented the LTD induction (CCG203769 n=6; CCG203769+MPEP n=6; p<0.05, Mann-Whitney test) (FIG. 7B).

Example 3

M4Rs Inhibited NMDA Receptor-mediated Synaptic Currents and $Ca^{2+}$ Transients In iSPNs, D2R signaling is not only necessary for LTD induction, but also prevents the induction of LTP (Higley and Sabatini, 2010; Shen et al., 2008; Chalifoux and Carter, 2010; Skeberdis et al., 2006; herein incorporated by reference in their entireties). dSPNs were filled with the $Ca^{2+}$-insensitive red fluorophore Alexa Fluor 568 and the $Ca^{2+}$-sensitive green fluorophore Fluo-5F to allow visualization of dendritic spines and simultaneous monitoring of NMDAR-mediated changes in intracellular $Ca^{2+}$ concentration (FIG. 3A); next, glutamate was uncaged at spine heads in the presence of the AMPA receptor (AMPAR) antagonist NBQX (10 µM) and the muscarinic receptor agonist muscarine (3 µM) while monitoring the postsynaptic response with and without the M4R PAM VU10010 (5 µM) (FIG. 3B). NMDAR-mediated $Ca^{2+}$ transients were not altered by the M4R PAM in this situation (n=10; p>0.05, Wilcoxon test) (FIG. 8). This negative result suggests that M4R signaling only affects NMDARs that have been positively modulated by D1R stimulation; D1R-mediated activation of protein kinase A (PKA) increases phosphorylation of the NMDAR NR2B subunit, enhancing receptor currents (Murphy et al., 2014; herein incorporated by reference in its entirety). To test this possibility, the D1R agonist SKF81297 (3 µM) was applied and then muscarine and the M4R PAM co-applied. M4R signaling decreased NMDAR-mediated Ca2+ transients by ~40% (n=12; p<0.05, Wilcoxon test) (FIG. 3B, C), in agreement with previous studies (Chalifoux and Carter, 2010; Higley and Sabatini, 2010; Skeberdis et al., 2006; herein incorporated by reference in their entireties).

In some neurons, it has been found that $Ca^{2+}$ permeability—but not total transmembrane current—is enhanced by phosphorylation of NMDARs (Chalifoux and Carter, 2010; Higley and Sabatini, 2010; herein incorporated by reference in their entireties). In other neurons, both $Ca^{2+}$ permeability and total current are modulated in parallel (Murphy et al., 2014; herein incorporated by reference in its entirety). To determine the situation in dSPNs, the effect of muscarine and VU10010 on NMDAR-mediated EPSCs evoked by uncaging glutamate on spine heads (uEPSCs) was examined in the presence of SKF81297. M4R signaling significantly reduced the amplitude of these postsynaptic NMDAR-mediated uEPSCs (n=8; p<0.05, Wilcoxon test) (FIG. 3D). In addition, muscarine (3 µM) reduced the amplitudes of NMDAR-mediated EPSCs evoked by local electrical stimulation and this modulation was augmented by VU10010 (5 µM) (muscarine n=10, muscarine+VU10010 n=10; p<0.05, Wilcoxon test) (FIG. 3E, F). These data show that dSPN M4R activation suppresses both total current and $Ca^{2+}$ influx at spine NMDARs.

Example 4

M4R Signaling Attenuated LTP Induction in dSPNs

Figure 4C:
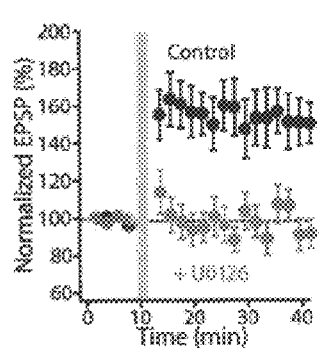
Figure 4D:
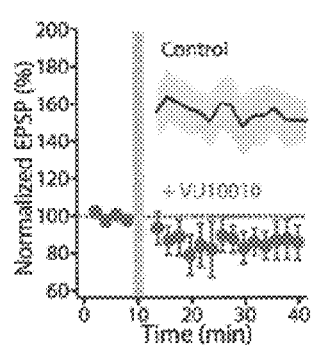

Pairing a presynaptic spike with a trailing postsynaptic spike induced a potent LTP in dSPNs (FIG. 4A, B, C) (Pawlak and Kerr, 2008; Shen et al., 2008; Yagishita et al., 2014; herein incorporated by reference in their entireties). This form of STDP LTP is dependent upon D1R signaling and $Ca^{2+}$ entry through NMDARs (Fino et al., 2010; Pawlak and Kerr, 2008; Shen et al., 2008; Yagishita et al., 2014; herein incorporated by reference in their entireties). One of the downstream targets of D1R and NMDAR signaling that has been implicated in LTP induction is extracellular signal-regulated kinase (ERK) (Park et al., 2014; Pascoli et al., 2012; Plotkin et al., 2014; herein incorporated by reference in their entireties). Inhibition of ERK with U0126 (10 µM) disrupted STDP LTP in dSPNs (control n=8; U0126 n=5; p<0.05, Mann-Whitney test) (FIG. 4C). Given its ability to antagonize D1R signaling and $Ca^{2+}$ entry through NMDARs, M4R stimulation should impede the induction of LTP in dSPNs. Boosting M4R signaling with the M4R PAM disrupted STDP LTP induction (control n=8; VU10010 n=6; p<0.05, Mann-Whitney test) (FIG. 4D).

Figure 4E:
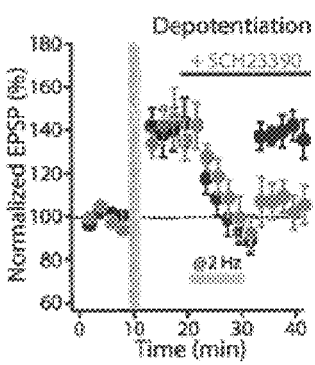
Figure 4F:
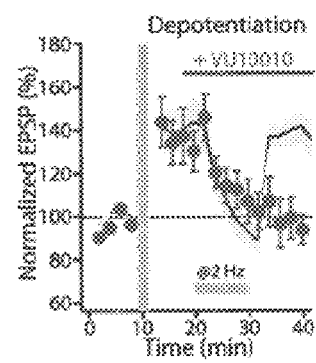

Shortly after LTP induction, synaptic strength is unstable. During this time, low-frequency afferent fiber stimulation (LFS; 2-5 Hz, 10 min) can reverse LTP; this reversal is called depotentiation (Otmakhova and Lisman, 1998; herein incorporated by reference in its entirety). Depotentiation is triggered by $Ca^{2+}$/calmodulin-mediated activation of protein phosphatase 2B (PP2B, or calcineurin); PP2B dephosphorylates DA and cAMP-regulated phosphoprotein of 32 kDa (DARPP-32), resulting in the dis-inhibition of protein phosphatase 1 (PP1) (Otmakhova and Lisman, 1998; Picconi et al., 2003; Zhuo et al., 1999; herein incorporated by reference in their entireties); PP1 dephosphorylates GluA subunits recently trafficked into the synaptic membrane during LTP expression, leading to their removal (Lee et al., 2000; herein incorporated by reference in its entirety). The serine residue on DARPP-32 targeted by PP2B is phosphorylated by PKA. 2 Hz intrastriatal stimulation that activated the axons of dopaminergic fibers did not depotentiate dSPN glutamatergic synapses (n=7; p>0.05, Wilcoxon test) (FIG. 4E). However, in the presence of the D1R antagonist SCH23390 (3 µM), the same protocol depotentiated glutamatergic EPSPs (control n=7; SCH23390 n=5; p<0.05, Mann-Whitney test) (FIG. 4E). Depotentiation also was achieved by addition of the M4R PAM VU10010 (5 µM; control n=7; VU10010 n=6; p<0.05, Mann-Whitney test) (FIG. 4F) (Picconi et al., 2006; herein incorporated by reference in its entirety).

Example 5

Aberrant Synaptic Plasticity in dSPNs was Corrected by an M4R PAM

Four to six weeks after a 6-hydroxydopamine (6-OHDA) lesion of the dopaminergic innervation of the striatum, conventional forms of striatal synaptic plasticity are lost (Picconi et al., 2003; herein incorporated by reference in its entirety). Although present shortly after lesioning (Shen et al., 2008; herein incorporated by reference in its entirety), STDP also was lost at longer survival times. In brain slices from D1-tdTomato and D2-eGFP BAC mice that had unilateral 6-OHDA lesions 3-4 weeks previously (FIG. 5A), repeated pairing of synaptic stimulation with a postsynaptic spike 5 ms later did not change EPSP amplitude in dSPNs (n=6; p>0.05, Wilcoxon test) (FIG. 5B) or iSPNs (n=5; p>0.05, Wilcoxon test) (FIG. 9).

Elevating striatal DA in lesioned rats by systemic administration of the DA precursor, L-DOPA, restores some forms of striatal synaptic plasticity (Belujon et al., 2010; Picconi et al., 2003; Thiele et al., 2014; herein incorporated by reference in their entireties). However, repeated L-DOPA treatment to parkinsonian rodents results in abnormal involuntary movements (AIMs), mimicking human LID (Cenci, 2007). In the rat LID model, high-frequency stimulation (HFS) of the striatum induces LTP at SPN glutamatergic synapses, but depotentiation of these synapses is disrupted (Picconi et al., 2003; herein incorporated by reference in its entirety). Experiments were conducted during development of embodiments described herein to determine whether either of these effects generalizes to STDP and whether these effects are specific to dSPNs or iSPNs. A mouse model of LID was generated in which dSPNs and iSPNs were labeled. One hour after the last injection of L-DOPA, mice were sacrificed and ex vivo brain slices were prepared for patch clamping recordings, two-photon laser-scanning microscopy and glutamate uncaging. In dSPNs from L-DOPA-treated mice, the standard pre/post STDP induction protocol led to a robust LTP (n=7; p<0.05, Wilcoxon test) (FIG. 5B). As in tissue from untreated mice, blocking ERK activity with U0126 prevented LTP induction—indicating that the plasticity was induced by the same mechanisms as in untreated mice (dyskinetic n=7; dyskinetic+U0126 n=5; p<0.05, Mann-Whitney test) (FIG. 5C).

However, in iSPNs from LID mice, the same STDP protocol induced LTD (6-OHDA n=5; L-DOPA n=5; p<0.05, Mann-Whitney test) (FIG. 9). These results demonstrate that synaptic plasticity in SPNs following L-DOPA treatment is not grossly abnormal and continues to be governed by SPN subtype. Moreover, enhancing M4R signaling with VU10010 blocked the induction of STDP LTP in dSPNs from LID mice (dyskinetic n=7; dyskinetic+ VU10010 n =6; p<0.05, Mann-Whitney test) (FIG. 5C), and reduced NMDAR-mediated Ca2+ transients (n=10; p<0.05, Wilcoxon test) (FIG. 5D, E), just as in naïve mice.

Intrastriatal LFS (2 Hz, 10 min) failed to depotentiate EPSPs in dSPNs from LID mice (n =5; p>0.05, Wilcoxon test) (FIG. 5F), indicating a deficit in the intracellular machinery underlying depotentiation. To if this is consequence of sustained D1R stimulation following the last L-DOPA dose, D1Rs were antagonized by bath application of SCH23390 and the LFS protocol repeated. In this situation, glutamatergic synapses depotentiated (dyskinetic n=5; dyskinetic+SCH23390 n=4; p<0.05, Mann-Whitney test) (FIG. 5F), indicating that the depotentiation machinery was intact. Boosting M4R signaling with the M4R PAM also restored depotentiation in the absence of a D1R antagonist (dyskinetic n=5; dyskinetic+VU10010 n=5; p<0.05, Mann-Whitney test) (FIG. 5F).

Example 6

M4R PAM Administration Reduced Dyskinetic Behavior

The data presented herein demonstrate that enhancing M4R signaling with a PAM blunts D1R-mediated LTP in dSPNs of LID models, both by diminishing LTP induction and by enabling depotentiation. To test whether striatal delivery of an M4R PAM in vivo attenuates LID-like behavior in mice, mice were unilaterally lesioned with 6-OHDA and given daily incremental doses of L-DOPA [1.5 mg/kg (days 1-3) and 3 mg/kg (days 4-8), intraperitoneally (i.p.)]; this regimen induced stable AIM scores within 4-5 days (Fasano et al., 2010; Francardo et al., 2011; herein incorporated by reference in their entireties). After LID induction, mice were treated with either L-DOPA or L-DOPA and VU152100 (20-120 mg/kg, i.p.) on days 6-8; VU152100 is an M4R PAM with improved pharmacokinetic properties than VU10010. VU152100 significantly attenuated L-DOPA-induced AIM scores (L-DOPA n=9; L-DOPA+VU152100 n=9; p<0.05, Mann-Whitney test) (FIG. 6A, B). Doubling the dose of VU152100 (120 mg/kg) did not increase the anti-dyskinetic effect (L-DOPA n=9; L-DOPA+VU152100 n =9; p<0.05, Mann-Whitney test) (FIG. 6B). The reduction in dyskinesia scores did not occur at the expense of the anti-parkinsonian action of L-DOPA as forelimb use asymmetry (Schallert et al., 2000; herein incorporated by reference in its entirety) was improved by L-DOPA alone or when co-administered with VU152100 (L-DOPA n=9, 47.98±2.41; L-DOPA+VU152100 n=9, 38.6±3.04; p>0.05, Mann-Whitney test). The co-administration of VU152100 also reduced the number of cells that were immunoreactive for the LID biochemical markers phosphorylated ERK1/2 (pERK1/2) and phosphorylated histone 3 (pH3) (Cenci and Konradi, 2010; Santini et al., 2009) compared to those given L-DOPA (pERK1/2: L-DOPA n=9; L-DOPA+VU152100 n=9; p<0.05; pH3: L-DOPA n=9; L-DOPA+VU152100 n=9; p<0.05, Mann-Whitney test) (FIG. 6C, D). Thus, systemic administration of an M4R PAM significantly diminished biomarkers associated with aberrant D1R signaling and LID-associated behaviors without compromising the therapeutic benefits of L-DOPA.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above by author last name, are herein incorporated by reference in their entireties.

Alexander, G. M., Rogan, S. C., Abbas, A. I., Armbruster, B. N., Pei, Y., Allen, J. A., Nonneman, R. J., Hartmann, J., Moy, S. S., Nicolelis, M. A., et al. (2009). Remote control of neuronal activity in transgenic mice expressing evolved G protein-coupled receptors. Neuron 63, 27-39.

Armbruster, B. N., Li, X., Pausch, M. H., Herlitze, S., and Roth, B. L. (2007). Evolving the lock to fit the key to create a family of G protein-coupled receptors potently activated by an inert ligand. Proc Natl Acad Sci USA 104, 5163-5168.

Augustin, S. M., Beeler, J. A., McGehee, D. S., and Zhuang, X. (2014). Cyclic AMP and afferent activity govern bidirectional synaptic plasticity in striatopallidal neurons. J Neurosci 34, 6692-6699.

Belujon, P., Lodge, D. J., and Grace, A. A. (2010). Aberrant striatal plasticity is specifically associated with dyskinesia following levodopa treatment. Mov Disord 25, 1568-1576.

Bernard, V., Normand, E., and Bloch, B. (1992). Phenotypical characterization of the rat striatal neurons expressing muscarinic receptor genes. J Neurosci 12, 3591-3600.

Bonsi, P., Martella, G., Cuomo, D., Platania, P., Sciamanna, G., Bernardi, G., Wess, J., and Pisani, A. (2008). Loss of muscarinic autoreceptor function impairs long-term depression but not long-term potentiation in the striatum. J Neurosci 28, 6258-6263.

Brady, A. E., Jones, C. K., Bridges, T. M., Kennedy, J. P., Thompson, A. D., Heiman, J. U., Breininger, M. L., Gentry, P. R., Yin, H., Jadhav, S. B., et al. (2008). Centrally active allosteric potentiators of the M4 muscarinic acetylcholine receptor reverse amphetamine-induced hyperlocomotor activity in rats. J Pharmacol Exp Ther 327, 941-953.

Calabresi, P., Picconi, B., Tozzi, A., and Di Filippo, M. (2007). Dopamine-mediated regulation of corticostriatal synaptic plasticity. Trends Neurosci 30, 211-219.

Caulfield, M. P., and Birdsall, N. J. (1998). International Union of Pharmacology. XVII. Classification of muscarinic acetylcholine receptors. Pharmacol Rev 50, 279-290.

Cenci, M. A. (2007). Dopamine dysregulation of movement control in L-DOPA-induced dyskinesia. Trends Neurosci 30, 236-243.

Cenci, M. A., and Konradi, C. (2010). Maladaptive striatal plasticity in L-DOPA-induced dyskinesia. Prog Brain Res 183, 209-233.

Cenci, M. A., and Lundblad, M. (2007). Ratings of L-DOPA-induced dyskinesia in the unilateral 6-OHDA lesion model of Parkinson's disease in rats and mice. Curr Protoc Neurosci Chapter 9, Unit 9.25-9.25.23.

Cerovic, M., Bagetta, V., Pendolino, V., Ghiglieri, V., Fasano, S., Morella, I., Hardingham, N., Heuer, A., Papale, A., Marchisella, F., et al. (2015). Derangement of Ras-guanine nucleotide-releasing factor 1 (Ras-GRF1) and extracellular signal-regulated kinase (ERK) dependent striatal plasticity in L-DOPA-induced dyskinesia. Biol Psychiatry 77, 106-115.

Chalifoux, J. R., and Carter, A. G. (2010). GABAB receptors modulate NMDA receptor calcium signals in dendritic spines. Neuron 66, 101-113.

Chan, C. S., Peterson, J. D., Gertler, T. S., Glajch, K. E., Quintana, R. E., Cui, Q., Sebel, L. E., Plotkin, J. L., Shen, W., Heiman, M., et al. (2012). Strain-specific regulation of striatal phenotype in Drd2-eGFP BAC transgenic mice. J Neurosci 32, 9124-9132.

Dencker, D., Weikop, P., Sørensen, G., Woldbye, D. P. D., Wörtwein, G., Wess, J., and Fink-Jensen, A. (2012). An allosteric enhancer of M4 muscarinic acetylcholine receptor function inhibits behavioral and neurochemical effects of cocaine. Psychopharmacology 224, 277-287.

Di Chiara, G., Morelli, M., and Consolo, S. (1994). Modulatory functions of neurotransmitters in the striatum: ACh/dopamine/NMDA interactions. Trends Neurosci 17, 228-233.

Ding, J. B., Guzman, J. N., Peterson, J. D., Goldberg, J. A., and Surmeier, D. J. (2010). Thalamic gating of corticostriatal signaling by cholinergic interneurons. Neuron 67, 294-307.

Fasano, S., Bezard, E., D'Antoni, A., Francardo, V., Indrigo, M., Qin, L., Dovero, S., Cerovic, M., Cenci, M. A., and Brambilla, R. (2010). Inhibition of Ras-guanine nucleotide-releasing factor 1 (Ras-GRF1) signaling in the striatum reverts motor symptoms associated with L-dopa-induced dyskinesia. Proc Natl Acad Sci USA 107, 21824-21829.

Ferguson, S. M., Eskenazi, D., Ishikawa, M., Wanat, M. J., Phillips, P. E. M., Dong, Y., Roth, B. L., and Neumaier, J. F. (2011). Transient neuronal inhibition reveals opposing roles of indirect and direct pathways in sensitization. Nat Neurosci 14, 22-24.

Feyder, M., Bonito-Oliva, A., and Fisone, G. (2011). L-DOPA-Induced dyskinesia and abnormal signaling in striatal medium spiny neurons: focus on dopamine D1 receptor-mediated transmission. Front Behav Neurosci 5, 71.

Fino, E., Paille, V., Cui, Y., Morera-Herreras, T., Deniau, J.-M., and Venance, L. (2010). Distinct coincidence detectors govern the corticostriatal spike timing-dependent plasticity. J Physiol 588, 3045-3062.

Francardo, V., Recchia, A., Popovic, N., Andersson, D., Nissbrandt, H., and Cenci, M. A. (2011). Impact of the lesion procedure on the profiles of motor impairment and molecular responsiveness to L-DOPA in the 6-hydroxydopamine mouse model of Parkinson's disease. Neurobiol Dis 42, 327-340.

Gerfen, C. R., and Surmeier, D. J. (2011). Modulation of striatal projection systems by dopamine. Annu Rev Neurosci 34, 441-466.

Gold, S. J., Ni, Y. G., Dohlman, H. G., and Nestler, E. J. (1997). Regulators of G-protein signaling (RGS) proteins: region-specific expression of nine subtypes in rat brain. J Neurosci 17, 8024-8037.

Gomeza, J., Zhang, L., Kostenis, E., Felder, C., Bymaster, F., Brodkin, J., Shannon, H., Xia, B., Deng, C., and Wess, J. (1999). Enhancement of D1 dopamine receptor-mediated locomotor stimulation in M4 muscarinic acetylcholine receptor knockout mice. Proc Natl Acad Sci USA 96, 10483-10488.

Gong, S., Zheng, C., Doughty, M. L., Losos, K., Didkovsky, N., Schambra, U. B., Nowak, N. J., Joyner, A., Leblanc, G., Hatten, M. E., et al. (2003). A gene expression atlas of the central nervous system based on bacterial artificial chromosomes. Nature 425, 917-925.

Heiman, M., Heilbut, A., Francardo, V., Kulicke, R., Fenster, R. J., Kolaczyk, E. D., Mesirov, J. P., Surmeier, D. J., Cenci, M. A., and Greengard, P. (2014). Molecular adaptations of striatal spiny projection neurons during levodopa-induced dyskinesia. Proc Natl Acad Sci USA 111, 4578-4583.

Hernández-Flores, T., Hernández-González, O., Pérez-Ramírez, M. B., Lara-González, E., Arias-García, M. A., Duhne, M., Pérez-Burgos, A., Prieto, G. A., Figueroa, A., Galarraga, E., et al. (2015). Modulation of direct pathway striatal projection neurons by muscarinic $M_4^-$type receptors. Neuropharmacology 89, 232-244.

Hersch, S. M., Gutekunst, C. A., Rees, H. D., Heilman, C. J., and Levey, A. I. (1994). Distribution of m1-m4 muscarinic receptor proteins in the rat striatum: light and electron microscopic immunocytochemistry using subtype-specific antibodies. J Neurosci 14, 3351-3363.

Hervé, D. (2011). Identification of a specific assembly of the g protein golf as a critical and regulated module of dopamine and adenosine-activated cAMP pathways in the striatum. Front Neuroanat 5, 48.

Higley, M. J., and Sabatini, B. L. (2010). Competitive regulation of synaptic Ca2+ influx by D2 dopamine and A2A adenosine receptors. Nat Neurosci 13, 958-966.

Higley, M. J., Soler-Llavina, G. J., and Sabatini, B. L. (2009). Cholinergic modulation of multivesicular release regulates striatal synaptic potency and integration. Nat Neurosci 12, 1121-1128.

Izzo, P. N., and Bolam, J. P. (1988). Cholinergic synaptic input to different parts of spiny striatonigral neurons in the rat. J Comp Neurol 269, 219-234.

Jenner, P. (2008). Molecular mechanisms of L-DOPA-induced dyskinesia. Nat Rev Neurosci 9, 665-677.

Jeon, J., Dencker, D., Wörtwein, G., Woldbye, D. P. D., Cui, Y., Davis, A. A., Levey, A. I., Schutz, G., Sager, T. N., Mörk, A., et al. (2010). A subpopulation of neuronal M4 muscarinic acetylcholine receptors plays a critical role in modulating dopamine-dependent behaviors. J Neurosci 30, 2396-2405.

Kozorovitskiy, Y., Saunders, A., Johnson, C. A., Lowell, B. B., and Sabatini, B. L. (2012). Recurrent network activity drives striatal synaptogenesis. Nature 485, 646-650.

Krapivinsky, G., Krapivinsky, L., Manasian, Y., Ivanov, A., Tyzio, R., Pellegrino, C., Ben-Ari, Y., Clapham, D. E., and Medina, I. (2003). The NMDA receptor is coupled to the ERK pathway by a direct interaction between NR2B and RasGRF1. Neuron 40, 775-784.

Kreitzer, A. C., and Malenka, R. C. (2007). Endocannabinoid-mediated rescue of striatal LTD and motor deficits in Parkinson's disease models. Nature 445, 643-647.

Kurz, A., Double, K. L., Lastres-Becker, I., Tozzi, A., Tantucci, M., Bockhart, V., Bonin, M., García-Arencibia, M., Nuber, S., Schlaudraff, F., et al. (2010). A53T-alpha-synuclein overexpression impairs dopamine signaling and striatal synaptic plasticity in old mice. PLoS ONE 5, e11464.

Lee, H. K., Barbarosie, M., Kameyama, K., Bear, M. F., and Huganir, R. L. (2000). Regulation of distinct AMPA receptor phosphorylation sites during bidirectional synaptic plasticity. Nature 405, 955-959.

Lerner, T. N., and Kreitzer, A. C. (2011). Neuromodulatory control of striatal plasticity and behavior. Curr Opin Neurobiol 21, 322-327.

Lerner, T. N., and Kreitzer, A. C. (2012). RGS4 is required for dopaminergic control of striatal LTD and susceptibility to parkinsonian motor deficits. Neuron 73, 347-359.

Lerner, T. N., Horne, E. A., Stella, N., and Kreitzer, A. C. (2010). Endocannabinoid signaling mediates psychomotor activation by adenosine A2A antagonists. J Neurosci 30, 2160-2164.

Loudon, J. M., Bromidge, S. M., Brown, F., Clark, M. S., Hatcher, J. P., Hawkins, J., Riley, G. J., Noy, G., and Orlek, B. S. (1997). SB 202026: a novel muscarinic partial agonist with functional selectivity for M1 receptors. J Pharmacol Exp Ther 283, 1059-1068.

Lovinger, D. M. (2010). Neurotransmitter roles in synaptic modulation, plasticity and learning in the dorsal striatum. Neuropharmacology 58, 951-961.

Maia, T. V., and Frank, M. J. (2011). From reinforcement learning models to psychiatric and neurological disorders. Nat Neurosci 14, 154-162.

Murphy, J. A., Stein, I. S., Lau, C. G., Peixoto, R. T., Aman, T. K., Kaneko, N., Aromolaran, K., Saulnier, J. L., Popescu, G. K., Sabatini, B. L., et al. (2014). Phosphorylation of Ser1166 on GluN2B by PKA is critical to synaptic NMDA receptor function and Ca2+ signaling in spines. J Neurosci 34, 869-879.

Nazzaro, C., Greco, B., Cerovic, M., Baxter, P., Rubino, T., Trusel, M., Parolaro, D., Tkatch, T., Benfenati, F., Pedarzani, P., et al. (2012). SK channel modulation rescues striatal plasticity and control over habit in cannabinoid tolerance. Nat Neurosci 15, 284-293.

Otmakhova, N. A., and Lisman, J. E. (1998). D1/D5 dopamine receptors inhibit depotentiation at CA1 synapses via cAMP-dependent mechanism. J Neurosci 18, 1270-1279.

Pancani, T., Bolarinwa, C., Smith, Y., Lindsley, C. W., Conn, P. J., and Xiang, Z. (2014). M4 mAChR-mediated modulation of glutamatergic transmission at corticostriatal synapses. ACS Chem Neurosci 5, 318-324.

Park, H., Popescu, A., and Poo, M.-M. (2014). Essential role of presynaptic NMDA receptors in activity-dependent BDNF secretion and corticostriatal LTP. Neuron 84, 1009-1022.

Pascoli, V., Turiault, M., and Lüscher, C. (2012). Reversal of cocaine-evoked synaptic potentiation resets drug-induced adaptive behaviour. Nature 481, 71-75.

Pavón, N., Martín, A. B., Mendialdua, A., and Moratalla, R. (2006). ERK phosphorylation and FosB expression are associated with L-DOPA-induced dyskinesia in hemiparkinsonian mice. Biol Psychiatry 59, 64-74.

Pawlak, V., and Kerr, J. N. D. (2008). Dopamine receptor activation is required for corticostriatal spike-timing-dependent plasticity. J Neurosci 28, 2435-2446.

Picconi, B., Centonze, D., Hakansson, K., Bernardi, G., Greengard, P., Fisone, G., Cenci, M. A., and Calabresi, P. (2003). Loss of bidirectional striatal synaptic plasticity in L-DOPA-induced dyskinesia. Nat Neurosci 6, 501-506.

Picconi, B., Passino, E., Sgobio, C., Bonsi, P., Barone, I., Ghiglieri, V., Pisani, A., Bernardi, G., Ammassari-Teule, M., and Calabresi, P. (2006). Plastic and behavioral abnormalities in experimental Huntington's disease: a crucial role for cholinergic interneurons. Neurobiol Dis 22, 143-152.

Plotkin, J. L., Day, M., Peterson, J. D., Xie, Z., Kress, G. J., Rafalovich, I., Kondapalli, J., Gertler, T. S., Flajolet, M., Greengard, P., et al. (2014). Impaired TrkB receptor signaling underlies corticostriatal dysfunction in Huntington's disease. Neuron 83, 178-188.

Rogan, S. C., and Roth, B. L. (2011). Remote control of neuronal signaling. Pharmacol Rev 63, 291-315.

Santini, E., Alcacer, C., Cacciatore, S., Heiman, M., Hervé, D., Greengard, P., Girault, J.-A., Valjent, E., and Fisone, G. (2009). L-DOPA activates ERK signaling and phosphorylates histone H3 in the striatonigral medium spiny neurons of hemiparkinsonian mice. J Neurochem 108, 621-633.

Santini, E., Valjent, E., Usiello, A., Carta, M., Borgkvist, A., Girault, J.-A., Hervé, D., Greengard, P., and Fisone, G. (2007). Critical involvement of cAMP/DARPP-32 and extracellular signal-regulated protein kinase signaling in L-DOPA-induced dyskinesia. J Neurosci 27, 6995-7005.

Sánchez, G., Colettis, N., Vázquez, P., Cerveñansky, C., Aguirre, A., Quillfeldt, J. A., Jerusalinsky, D., and Kornisiuk, E. (2009). Muscarinic inhibition of hippocampal and striatal adenylyl cyclase is mainly due to the M4 receptor. Neurochem Res 34, 1363-1371.

Schallert, T., Fleming, S. M., Leasure, J. L., Tillerson, J. L., and Bland, S. T. (2000). CNS plasticity and assessment of forelimb sensorimotor outcome in unilateral rat models of stroke, cortical ablation, parkinsonism and spinal cord injury. Neuropharmacology 39, 777-787.

Shen, W., Flajolet, M., Greengard, P., and Surmeier, D. J. (2008). Dichotomous dopaminergic control of striatal synaptic plasticity. Science 321, 848-851.

Shen, W., Hamilton, S. E., Nathanson, N. M., and Surmeier, D. J. (2005). Cholinergic suppression of KCNQ channel currents enhances excitability of striatal medium spiny neurons. J Neurosci 25, 7449-7458.

Shen, W., Tian, X., Day, M., Ulrich, S., Tkatch, T., Nathanson, N. M., and Surmeier, D. J. (2007). Cholinergic modulation of Kir2 channels selectively elevates dendritic excitability in striatopallidal neurons. Nat Neurosci 10, 1458-1466.

Shirey, J. K., Xiang, Z., Orton, D., Brady, A. E., Johnson, K. A., Williams, R., Ayala, J. E., Rodriguez, A. L., Wess, J., Weaver, D., et al. (2008). An allosteric potentiator of M4 mAChR modulates hippocampal synaptic transmission. Nat Chem Biol 4, 42-50.

Shuen, J. A., Chen, M., Gloss, B., and Calakos, N. (2008). Drd1a-tdTomato BAC transgenic mice for simultaneous visualization of medium spiny neurons in the direct and indirect pathways of the basal ganglia. J Neurosci 28, 2681-2685.

Skeberdis, V. A., Chevaleyre, V., Lau, C. G., Goldberg, J. H., Pettit, D. L., Suadicani, S. O., Lin, Y., Bennett, M. V. L., Yuste, R., Castillo, P. E., et al. (2006). Protein kinase A regulates calcium permeability of NMDA receptors. Nat Neurosci 9, 501-510.

Surmeier, D. J., Plotkin, J., and Shen, W. (2009). Dopamine and synaptic plasticity in dorsal striatal circuits controlling action selection. Curr Opin Neurobiol 19, 621-628.

Sweatt, J. D. (2004). Mitogen-activated protein kinases in synaptic plasticity and memory. Curr Opin Neurobiol 14, 311-317.

Thiele, S. L., Chen, B., Lo, C., Gertler, T. S., Warre, R., Surmeier, J. D., Brotchie, J. M., and Nash, J. E. (2014). Selective loss of bi-directional synaptic plasticity in the direct and indirect striatal output pathways accompanies generation of parkinsonism and L-DOPA induced dyskinesia in mouse models. Neurobiol Dis 71C, 334-344.

Threlfell, S., Clements, M. A., Khodai, T., Pienaar, I. S., Exley, R., Wess, J., and Cragg, S. J. (2010). Striatal muscarinic receptors promote activity dependence of dopamine transmission via distinct receptor subtypes on cholinergic interneurons in ventral versus dorsal striatum. J Neurosci 30, 3398-3408.

Tillerson, J. L., Cohen, A. D., Philhower, J., Miller, G. W., Zigmond, M. J., and Schallert, T. (2001). Forced limb-use effects on the behavioral and neurochemical effects of 6-hydroxydopamine. J Neurosci 21, 4427-4435.

Tozzi, A., de Iure, A., Di Filippo, M., Tantucci, M., Costa, C., Borsini, F., Ghiglieri, V., Giampá, C., Fusco, F. R., Picconi, B., et al. (2011). The distinct role of medium spiny neurons and cholinergic interneurons in the D$_2$/A$_2$A receptor interaction in the striatum: implications for Parkinson's disease. J Neurosci 31, 1850-1862.

Wang, Z., Kai, L., Day, M., Ronesi, J., Yin, H. H., Ding, J., Tkatch, T., Lovinger, D. M., and Surmeier, D. J. (2006). Dopaminergic control of corticostriatal long-term synaptic depression in medium spiny neurons is mediated by cholinergic interneurons. Neuron 50, 443-452.

Wess, J., Nakajima, K., and Jain, S. (2013). Novel designer receptors to probe GPCR signaling and physiology. Trends Pharmacol Sci 34, 385-392.

Westin, J. E., Vercammen, L., Strome, E. M., Konradi, C., and Cenci, M. A. (2007). Spatiotemporal pattern of striatal ERK1/2 phosphorylation in a rat model of L-DOPA-induced dyskinesia and the role of dopamine D1 receptors. Biol Psychiatry 62, 800-810.

Wickens, J. R., Reynolds, J. N. J., and Hyland, B. I. (2003). Neural mechanisms of reward-related motor learning. Curr Opin Neurobiol 13, 685-690.

Wu, Y.-W., Kim, J.-I., Tawfik, V. L., Lalchandani, R. R., Scherrer, G., and Ding, J. B. (2015). Input- and cell-type-specific endocannabinoid-dependent LTD in the striatum. Cell Rep 10, 75-87.

Yagishita, S., Hayashi-Takagi, A., Ellis-Davies, G. C. R., Urakubo, H., Ishii, S., and Kasai, H. (2014). A critical time window for dopamine actions on the structural plasticity of dendritic spines. Science 345, 1616-1620.

Yin, H. H., and Knowlton, B. J. (2006). The role of the basal ganglia in habit formation. Nat Rev Neurosci 7, 464-476.

Yin, H. H., and Lovinger, D. M. (2006). Frequency-specific and D2 receptor-mediated inhibition of glutamate release by retrograde endocannabinoid signaling. Proc Natl Acad Sci USA 103, 8251-8256.

Zhu, J. J., Qin, Y., Zhao, M., van Aelst, L., and Malinow, R. (2002). Ras and Rap control AMPA receptor trafficking during synaptic plasticity. Cell 110, 443-455.

Zhuo, M., Zhang, W., Son, H., Mansuy, I., Sobel, R. A., Seidman, J., and Kandel, E. R. (1999). A selective role of calcineurin aalpha in synaptic depotentiation in hippocampus. Proc Natl Acad Sci USA 96, 4650-4655.

The invention claimed is:

1. A method of treating a psychomotor disease comprising co-administering levodopa and a 4 muscarinic receptor (M4R) positive allosteric modulator (PAM) to a subject.

2. The method of claim 1, wherein the psychomotor disease is Parkinson's disease (PD).

3. The method of claim 1, wherein the levodopa and M4R-PAM are administered simultaneously.

4. The method of claim 3, wherein the levodopa and M4R-PAM are co-formulated.

5. The method of claim 1, wherein the levodopa and M4R-PAM are administered sequentially and in separate pharmaceutical formulations.

6. The method of claim 1, wherein the M4R-PAM is a small molecule.

7. The method of claim 6, wherein the M4R-PAM is selected from the group consisting of VU0467154, VU010010, and VU152100.

8. A method of treating levodopa-induced dyskinesias (LID) in a subject being treated with levodopa comprising administering an M4R PAM.

9. The method of claim 8, wherein the psychomotor disease is Parkinson's disease (PD).

10. The method of claim 8, wherein the levodopa and M4R-PAM are administered simultaneously.

11. The method of claim 10, wherein the levodopa and M4R-PAM are co-formulated.

12. The method of claim 8, wherein the levodopa and M4R-PAM are administered sequentially and in separate pharmaceutical formulations.

13. The method of claim 8, wherein the M4R-PAM is a small molecule.

14. The method of claim 13, wherein the M4R-PAM is selected from the group consisting of VU0467154, VU010010, and VU152100.

* * * * *